(12) United States Patent
Bundra et al.

(10) Patent No.: US 12,121,384 B2
(45) Date of Patent: Oct. 22, 2024

(54) SYSTEMS AND METHODS FOR X-RAY IMAGING TISSUE SPECIMENS

(71) Applicant: HOLOGIC, INC., Marlborough, MA (US)

(72) Inventors: Filip Nikolas Bundra, Marlborough, MA (US); Christine Janssen, Marlborough, MA (US); Zhenxue Jing, Marlborough, MA (US); Tarpit Patel, Marlborough, MA (US); Thomas Deyoung, Marlborough, MA (US)

(73) Assignee: Hologic, Inc., Marlborough, MA (US)

( * ) Notice: Subject to any disclaimer, the term of this patent is extended or adjusted under 35 U.S.C. 154(b) by 203 days.

(21) Appl. No.: 17/910,681

(22) PCT Filed: Mar. 30, 2021

(86) PCT No.: PCT/US2021/024784
§ 371 (c)(1),
(2) Date: Sep. 9, 2022

(87) PCT Pub. No.: WO2021/202455
PCT Pub. Date: Oct. 7, 2021

(65) Prior Publication Data
US 2023/0172572 A1    Jun. 8, 2023

Related U.S. Application Data

(60) Provisional application No. 63/002,898, filed on Mar. 31, 2020.

(51) Int. Cl.
*A61B 6/06* (2006.01)
*A61B 6/04* (2006.01)
(Continued)

(52) U.S. Cl.
CPC ............ *A61B 6/502* (2013.01); *A61B 6/0414* (2013.01); *A61B 6/06* (2013.01); *A61B 6/4035* (2013.01);
(Continued)

(58) Field of Classification Search
CPC ......... A61B 6/502; A61B 6/0414; A61B 6/06; A61B 6/4035; A61B 10/0283; G21K 1/025
See application file for complete search history.

(56) References Cited

U.S. PATENT DOCUMENTS

| 4,038,988 A | 8/1977 | Perisse |
| 4,134,012 A | 1/1979 | Smallbone et al. |

(Continued)

FOREIGN PATENT DOCUMENTS

| DE | 20 2019 106 995 U1 | 1/2020 |
| EP | 2007287 | 6/2016 |

(Continued)

OTHER PUBLICATIONS

International Search Report and Written Opinion of the International Searching Authority for International Patent Application No. PCT/US2021/024784 mailed Jul. 7, 2021, 12 pages.

(Continued)

*Primary Examiner* — David P Porta
*Assistant Examiner* — Fani Polyzos Boosalis
(74) *Attorney, Agent, or Firm* — Merchant & Gould P.C.

(57) ABSTRACT

An x-ray breast imaging system includes a breast support platform including an x-ray receptor, and an x-ray tube head. The x-ray tube head includes an x-ray source configured to emit an x-ray beam in a direction towards the x-ray receptor, and a collimator. A filter assembly including a plurality of filter slots selectively positionable adjacent to the collimator, and a specimen imaging filter disposed within a slot of the (Continued)

plurality of filter slots. The specimen imaging filter includes at least one aperture defined therein. The specimen imaging filter also blocks a portion of the emitted x-ray beam so that the at least one aperture defines a path of the emitted x-ray beam towards the x-ray receptor.

23 Claims, 12 Drawing Sheets

(51) Int. Cl.
    *A61B 6/40*     (2024.01)
    *A61B 6/50*     (2024.01)
    *A61B 10/02*     (2006.01)
    *G21K 1/02*     (2006.01)

(52) U.S. Cl.
    CPC .......... *A61B 10/0283* (2013.01); *G21K 1/025* (2013.01)

(56) References Cited

U.S. PATENT DOCUMENTS

| | | |
|---|---|---|
| 4,306,570 A | 12/1981 | Matthews |
| 4,549,554 A | 10/1985 | Markham |
| 4,658,834 A | 4/1987 | Blankenship et al. |
| 4,802,195 A | 1/1989 | Wojcienchowski |
| 4,803,639 A | 2/1989 | Steele |
| 4,837,795 A | 6/1989 | Garrigus |
| 4,852,560 A | 8/1989 | Hermann, Jr. |
| 5,023,894 A | 6/1991 | Yamashita |
| 5,023,895 A | 6/1991 | McCroskey |
| 5,256,160 A | 10/1993 | Clement |
| 5,427,742 A | 6/1995 | Holland |
| 5,456,689 A | 10/1995 | Kresch et al. |
| 5,491,344 A | 2/1996 | Kenny et al. |
| 5,505,210 A | 4/1996 | Clement |
| 5,526,822 A | 6/1996 | Burbank et al. |
| 5,541,856 A | 7/1996 | Hammermeister |
| 5,575,293 A | 11/1996 | Miller et al. |
| 5,609,827 A | 3/1997 | Russell |
| 5,754,621 A | 5/1998 | Suzuki |
| 5,983,125 A | 11/1999 | Alfano et al. |
| 6,017,316 A | 1/2000 | Ritchart et al. |
| 6,032,673 A | 3/2000 | Savage et al. |
| 6,058,159 A | 5/2000 | Conway |
| 6,163,590 A | 12/2000 | Wilkins |
| 6,207,111 B1 | 3/2001 | Weinberg |
| 6,225,107 B1 | 5/2001 | Nagle |
| 6,234,672 B1 | 5/2001 | Tomasetti et al. |
| 6,322,522 B1 | 11/2001 | Zimmon |
| 6,403,035 B1 | 6/2002 | Caratsch et al. |
| 6,485,436 B1 | 11/2002 | Truckai et al. |
| 6,535,284 B1 | 3/2003 | Hajduk et al. |
| 6,646,721 B2 | 11/2003 | Compter |
| 6,899,850 B2 | 5/2005 | Haywood |
| 7,166,113 B2 | 1/2007 | Arambula |
| 7,175,612 B2 | 2/2007 | Felix et al. |
| 7,397,894 B2 | 7/2008 | Nakai |
| 7,546,925 B1 | 6/2009 | Zuk, Jr. |
| 7,616,801 B2 | 11/2009 | Gkanatsios et al. |
| 7,662,109 B2 | 2/2010 | Hibner |
| 7,692,144 B2 | 4/2010 | Watanabe |
| 7,715,523 B2 | 5/2010 | Lafferty |
| 7,753,857 B2 | 7/2010 | Hibner |
| 7,758,601 B2 | 7/2010 | Heywang-Koebrunner et al. |
| 7,854,705 B2 | 12/2010 | Pawluczyk et al. |
| 7,856,081 B2 | 12/2010 | Peschmann |
| 7,858,038 B2 | 12/2010 | Andreyko et al. |
| 7,867,173 B2 | 1/2011 | Hibner et al. |
| 7,869,563 B2 | 1/2011 | DeFreitas et al. |
| 7,881,428 B2 | 2/2011 | Jing et al. |
| 7,972,062 B2 | 7/2011 | Nicolosi |
| 8,038,347 B2 | 10/2011 | Manak |
| 8,038,627 B2 | 10/2011 | Hibner |
| 8,050,735 B2 | 11/2011 | Feke |
| 8,052,616 B2 | 11/2011 | Andrisek et al. |
| 8,162,140 B2 | 4/2012 | Hansen |
| 8,177,728 B2 | 5/2012 | Hibner et al. |
| 8,213,570 B2 | 7/2012 | Panesar |
| 8,217,357 B2 | 7/2012 | Stein et al. |
| 8,235,913 B2 | 8/2012 | Hibner et al. |
| 8,284,896 B2 | 10/2012 | Singh |
| 8,532,745 B2 | 9/2013 | DeFreitas et al. |
| 8,565,374 B2 | 10/2013 | DeFreitas et al. |
| 8,702,623 B2 | 4/2014 | Parihar |
| 8,741,232 B2 | 6/2014 | Baysal |
| 8,764,679 B2 | 7/2014 | Miller et al. |
| 8,787,522 B2 | 7/2014 | Smith et al. |
| 8,873,716 B2 | 10/2014 | Ren et al. |
| 8,911,381 B2 | 12/2014 | Hibner et al. |
| 8,923,603 B2 | 12/2014 | Weston |
| 8,956,306 B2 | 2/2015 | Hibner |
| 8,971,484 B2 | 3/2015 | Beckmann |
| 8,983,030 B2 | 3/2015 | Ookawa |
| 9,020,579 B2 | 4/2015 | Smith et al. |
| 9,066,706 B2 | 6/2015 | DeFreitas et al. |
| 9,068,920 B2 | 6/2015 | Churilla |
| 9,129,715 B2 | 9/2015 | Adler |
| 9,188,696 B2 | 11/2015 | Schafer |
| 9,234,855 B2 | 1/2016 | Watanabe |
| 9,277,895 B2 | 3/2016 | Hara |
| 9,322,790 B2 | 4/2016 | Ookawa |
| 9,326,755 B2 | 5/2016 | Fiebig |
| 9,329,139 B2 | 5/2016 | Itou |
| 9,341,546 B2 | 5/2016 | Stuke |
| 9,347,894 B2 | 5/2016 | Sims |
| 9,492,130 B2 | 11/2016 | Flagle et al. |
| 9,498,175 B2 | 11/2016 | Stein et al. |
| 9,549,709 B2 | 1/2017 | DeFreitas et al. |
| 9,557,281 B2 | 1/2017 | Badawi et al. |
| 9,642,581 B2 | 5/2017 | Lowe |
| 9,668,711 B2 | 6/2017 | Smith et al. |
| 9,733,167 B2 | 8/2017 | Wismueller |
| 9,865,424 B2 | 1/2018 | Ikeda |
| 9,901,320 B2 | 2/2018 | DeFreitas et al. |
| 9,943,850 B2 | 4/2018 | Purdy |
| 9,953,799 B2 | 4/2018 | Hakoda |
| 10,008,298 B2 | 6/2018 | King |
| 10,010,296 B2 | 7/2018 | Basu |
| 10,078,093 B2 | 7/2018 | Flagle |
| 10,098,216 B2 | 10/2018 | Kabumoto |
| 10,105,709 B2 | 10/2018 | Purdy |
| 10,145,806 B2 | 12/2018 | Tanaka |
| 10,190,997 B2 | 1/2019 | Aoki |
| 10,194,875 B2 | 2/2019 | DeFreitas et al. |
| 10,201,331 B2 | 2/2019 | Fleming |
| 10,322,412 B2 | 6/2019 | Purdy |
| 10,393,678 B2 | 8/2019 | Watanabe |
| 10,488,351 B2 | 11/2019 | Butani |
| 10,489,964 B2 | 11/2019 | Wang |
| 10,561,387 B2 | 2/2020 | Smith et al. |
| 10,631,809 B2 * | 4/2020 | Noh ........................ A61B 6/44 |
| 10,705,030 B2 | 7/2020 | Watanabe |
| 10,709,396 B2 * | 7/2020 | Lou ........................ A61B 6/032 |
| 10,729,403 B2 | 8/2020 | DeFreitas et al. |
| 10,753,836 B2 | 8/2020 | O'Driscoll |
| 10,792,003 B2 | 10/2020 | Smith et al. |
| 10,809,208 B2 | 10/2020 | Yashima |
| 10,905,385 B2 | 2/2021 | DeFreitas et al. |
| 11,083,426 B2 | 8/2021 | DeFreitas |
| 11,191,502 B2 | 12/2021 | Smith et al. |
| 11,246,551 B2 | 2/2022 | Butani |
| 11,317,881 B2 | 5/2022 | Purdy |
| 11,358,149 B2 | 6/2022 | Purdy |
| 11,478,206 B2 | 10/2022 | Smith et al. |
| 11,566,981 B2 | 1/2023 | O'Driscoll |
| 11,617,548 B2 | 4/2023 | DeFreitas et al. |
| 11,730,434 B2 | 8/2023 | DeFreitas |
| 11,877,877 B2 | 1/2024 | Purdy |
| 2002/0007188 A1 | 1/2002 | Arambula |
| 2002/0145722 A1 | 10/2002 | Compter |
| 2002/0193656 A1 | 12/2002 | Ravins et al. |
| 2003/0087423 A1 | 5/2003 | Haywood |

(56) References Cited

U.S. PATENT DOCUMENTS

| | | |
|---|---|---|
| 2003/0216730 A1 | 11/2003 | Barry et al. |
| 2004/0022350 A1 | 2/2004 | Gregerson et al. |
| 2004/0174031 A1 | 9/2004 | Rasmussen |
| 2004/0218716 A1 | 11/2004 | Freifeld |
| 2005/0051723 A1 | 3/2005 | Neagle et al. |
| 2005/0065453 A1 | 3/2005 | Shabaz et al. |
| 2005/0112034 A1 | 5/2005 | McCormick |
| 2005/0124913 A1 | 6/2005 | Damarati |
| 2005/0148842 A1 | 7/2005 | Wang |
| 2006/0074343 A1 | 4/2006 | Hibner |
| 2006/0116603 A1 | 6/2006 | Shibazaki et al. |
| 2006/0173266 A1 | 8/2006 | Pawluczyk et al. |
| 2007/0106176 A1 | 5/2007 | Mark et al. |
| 2007/0116612 A1 | 5/2007 | Williamson |
| 2007/0166834 A1 | 7/2007 | Williamson, IV et al. |
| 2007/0237684 A1 | 10/2007 | Hansen |
| 2007/0239067 A1 | 10/2007 | Hibner et al. |
| 2007/0270714 A1 | 11/2007 | Cushner et al. |
| 2008/0004545 A1 | 1/2008 | Garrison |
| 2008/0082021 A1 | 4/2008 | Ichikawa |
| 2008/0132805 A1 | 6/2008 | Heywang-Koebrunner et al. |
| 2008/0214955 A1 | 9/2008 | Speeg et al. |
| 2008/0221480 A1 | 9/2008 | Hibner et al. |
| 2008/0228103 A1 | 9/2008 | Ritchie et al. |
| 2008/0249434 A1 | 10/2008 | Hashimshony et al. |
| 2009/0088663 A1 | 4/2009 | Miller et al. |
| 2009/0088666 A1 | 4/2009 | Miller et al. |
| 2009/0131818 A1 | 5/2009 | Speeg et al. |
| 2009/0131820 A1 | 5/2009 | Speeg |
| 2009/0131823 A1 | 5/2009 | Andreyko et al. |
| 2009/0171243 A1 | 7/2009 | Hibner et al. |
| 2009/0171244 A1 | 7/2009 | Ning |
| 2009/0213987 A1 | 8/2009 | Stein |
| 2010/0080346 A1 | 4/2010 | Kalender et al. |
| 2010/0081964 A1 | 4/2010 | Mark |
| 2010/0152611 A1 | 6/2010 | Parihar |
| 2010/0160824 A1 | 6/2010 | Parihar |
| 2010/0160826 A1 | 6/2010 | Parihar |
| 2010/0191145 A1 | 7/2010 | Lafferty |
| 2010/0317997 A1 | 12/2010 | Hibner |
| 2011/0142201 A1 | 6/2011 | Eberhard et al. |
| 2011/0285837 A1 | 11/2011 | Bello |
| 2012/0014504 A1 | 1/2012 | Jang et al. |
| 2012/0051514 A1 | 3/2012 | Sims et al. |
| 2012/0053484 A1 | 3/2012 | Parks |
| 2012/0116246 A1 | 5/2012 | Hibner |
| 2012/0123295 A1 | 5/2012 | Sanbuichi |
| 2012/0245485 A1 | 9/2012 | Hibner |
| 2013/0053724 A1 | 2/2013 | Fiebig |
| 2013/0231585 A1 | 9/2013 | Flagle |
| 2014/0039343 A1 | 2/2014 | Mescher |
| 2014/0051986 A1 | 2/2014 | Zhao et al. |
| 2014/0065656 A1 | 3/2014 | Baysal |
| 2014/0072104 A1 | 3/2014 | Jacobsen et al. |
| 2014/0198893 A1 | 7/2014 | Badawi et al. |
| 2014/0257135 A1 | 9/2014 | DeFreitas |
| 2014/0276209 A1 | 9/2014 | Hibner |
| 2015/0083893 A1 | 3/2015 | Wismueller |
| 2015/0131773 A1 | 5/2015 | Lowe et al. |
| 2015/0209017 A1 | 7/2015 | Fleming |
| 2016/0211045 A1 | 7/2016 | Jeon et al. |
| 2017/0131311 A1 | 5/2017 | Flagle |
| 2017/0309063 A1 | 10/2017 | Wang |
| 2017/0336706 A1 | 11/2017 | Wang |
| 2018/0249985 A1 | 9/2018 | DeFreitas et al. |
| 2019/0054217 A1 | 2/2019 | Axon |
| 2019/0072463 A1 | 3/2019 | O'Driscoll |
| 2019/0167869 A1 | 6/2019 | Willard |
| 2019/0285558 A1 | 9/2019 | DeFreitas |
| 2019/0346471 A1 | 11/2019 | Flagle |
| 2020/0029927 A1 | 1/2020 | Wilson et al. |
| 2020/0061622 A1 | 2/2020 | Purdy |
| 2020/0085393 A1 | 3/2020 | Zhang et al. |
| 2020/0187923 A1 | 6/2020 | Safir |
| 2020/0268331 A1 | 8/2020 | Purdy |
| 2020/0352543 A1 | 11/2020 | DeFreitas et al. |
| 2020/0386657 A1 | 12/2020 | O'Driscoll |
| 2022/0015729 A1 | 1/2022 | Purdy et al. |
| 2022/0039766 A1 | 2/2022 | DeFreitas |
| 2022/0110597 A1 | 4/2022 | Chen |
| 2022/0133252 A1 | 5/2022 | Smith et al. |
| 2022/0331808 A1 | 10/2022 | Purdy |
| 2023/0012310 A1 | 1/2023 | Stango |
| 2023/0014922 A1 | 1/2023 | DeFreitas |
| 2023/0121010 A1 | 4/2023 | Smith et al. |
| 2023/0136395 A1 | 5/2023 | Chen |
| 2023/0204473 A1 | 6/2023 | O'Driscoll |
| 2023/0355200 A1 | 11/2023 | Ren |
| 2023/0404499 A1 | 12/2023 | DeFreitas |
| 2024/0016461 A1 | 1/2024 | Wolff |

FOREIGN PATENT DOCUMENTS

| | | |
|---|---|---|
| GB | 2018601 | 10/1979 |
| JP | 2014-526937 | 10/2014 |
| JP | 2015-085056 | 5/2015 |
| JP | 2015-520402 | 7/2015 |
| JP | 2016-154878 | 9/2016 |
| JP | 2017099928 | 6/2017 |
| WO | 8101363 | 5/1981 |
| WO | 2007021905 | 2/2007 |
| WO | 2008/025146 | 3/2008 |
| WO | 2009/120206 | 10/2009 |
| WO | 2010/028208 | 3/2010 |
| WO | 2011/140374 | 11/2011 |
| WO | 2012/074885 | 6/2012 |
| WO | 2013/166497 | 11/2013 |
| WO | 2017/060726 | 4/2017 |
| WO | 2018/183086 | 10/2018 |
| WO | 2018/204710 | 11/2018 |
| WO | 2019/051496 | 3/2019 |
| WO | 2019/085342 | 5/2019 |
| WO | 2019/216766 | 11/2019 |
| WO | 2020/106888 | 5/2020 |
| WO | 2021/202455 | 10/2021 |

OTHER PUBLICATIONS

Watanabe, M et al., "The quantitative analysis of thin specimens: a review of progress from the Cliff-Lorimer to the new zeta-factor methods", Journal of Microscopy, vol. 221, No. 2, Feb. 1, 2006, p. 91.

Basak Erguvan-Dogan et al., "Specimen Radiography in Confirmation of MRI-Guided Needle Localization and Surgical Excision of Breast Lesions", American Journal of Roentgenology, American Roentgen Ray Society, vol. 187, No. 2: 339-344 (2006).

PCT International Preliminary Report on Patentability in Application PCT/US2021/024784, mailed Oct. 13, 2022, 9 pages.

\* cited by examiner

SYSTEMS AND METHODS FOR X-RAY IMAGING TISSUE SPECIMENS

This application is a National Stage Application of PCT/US2021/024784, filed Mar. 30, 2021, which claims the benefit of priority to U.S. Provisional Patent Application Ser. No. 63/002,898, filed Mar. 31, 2020, the entire disclosures of which are incorporated by reference in their entireties. To the extent appropriate, a claim of priority is made to each of the above disclosed applications.

BACKGROUND

Breast imaging processes, including mammography, tomosynthesis, and computed tomography, capture x-ray images of the breast to screen for breast cancer. The breast imaging processes involve compression of the breast between surfaces of a breast support platform and a compression paddle prior to and during image capture. Compression serves a number of purposes, including to: (1) make the breast thinner in the direction of x-ray flux and thereby reduces patient radiation exposure from the level required to image the thicker parts of a breast that are not compressed; (2) make the breast more uniform in thickness in the direction of x-ray flux and thereby facilitates more uniform exposure at the image plane over the entire breast image; (3) immobilize the breast during the x-ray exposure and thereby reduces image blurring; and (4) bring breast tissues out from the chest wall into the imaging exposure field and thus allows for more tissue imaging.

Standard compression methods for mammography and tomosynthesis use a movable, rigid, radiolucent compression paddle. The breast is placed in an imaging area on the breast support platform that typically is flat, and the paddle then compresses the breast, usually while a technologist or other health professional is holding the breast in place. The technologist may also manipulate the breast to ensure proper tissue coverage in the image receptor's field of view. Furthermore, once the breast is immobilized, tissue specimens may be obtained for analysis, for example, by a biopsy procedure.

One known challenge with tissue specimens is how to image them once obtained. For example, the tissue specimens may be imaged to provide verification that the required or desired tissue was correctly obtained. In another example, the tissue specimens may be imaged for further diagnostic procedures. At least some known tissue specimen imaging systems are separate systems from the breast imaging system. As such, two imaging systems must be maintained and the technologist must work between the two while the patient's breast remains compressed, thereby increasing patient discomfort. Other tissue specimen imaging systems may be attached to the breast imaging system, however, these systems often provide undesirable image quality.

SUMMARY

In one aspect, the technology relates to an x-ray breast imaging system including: a breast support platform including an x-ray receptor; and an x-ray tube head including: an x-ray source configured to emit an x-ray beam in a direction towards the x-ray receptor; a collimator; a filter assembly including a plurality of filter slots selectively positionable adjacent to the collimator; and a specimen imaging filter disposed within a slot of the plurality of filter slots, wherein the specimen imaging filter includes at least one aperture defined therein, and wherein the specimen imaging filter blocks a portion of the emitted x-ray beam so that the at least one aperture defines a path of the emitted x-ray beam towards the x-ray receptor.

In the example, at least one aperture is substantially rectangular-shaped. In another example, the specimen imaging filter is formed from lead material. In yet another example, the at least one aperture includes a pair of apertures. In still another example, the collimator includes at least one collimator blade, and the at least one collimator blade is configured to selectively cover one of the pair of apertures. In yet another example, the filter assembly includes a rotatable filter wheel having the plurality of filter slots. In an example, the x-ray source includes three or more focal spot sizes.

In another example, one of the focal spot sizes is less than or equal to 50 µm. In yet another example, the system further includes a specimen container configured to retain one or more tissue specimens. In still another example, the specimen container is removably coupleable to the imaging system and independently rotatable relative to the x-ray tube head. In an example, the at least one aperture defines the path of the emitted x-ray beam that corresponds to a specific area on the breast support platform. In another example, the system further includes a compression paddle configured to compress a patient's breast against the breast support platform, and the at least one aperture defines the path of the emitted x-ray beam that corresponds to a specific area on the compression paddle.

In yet another example, the system further includes a vacuum assisted biopsy assembly coupled to the imaging system, and the vacuum assisted biopsy assembly includes a reservoir configured to capture a tissue specimen. In still another example, the system further includes a high energy acquisition filter formed from copper.

In another aspect, the technology relates to a method of acquiring a tissue specimen image on an x-ray breast imaging system, the method including: compressing a patient's breast between a compression paddle and a support platform; imaging the patient's breast via an x-ray source disposed in an x-ray tube head and an x-ray receptor disposed in the support platform; obtaining one or more tissue specimens from the patient's breast; retaining the one or more tissue specimens in a container; imaging the one or more tissue specimens via the same x-ray source and x-ray receptor used for imaging the patient's breast, wherein the imaging includes blocking a portion of an emitted x-ray beam from the x-ray source by a specimen imaging filter within the x-ray tube head so that at least one aperture within the specimen imaging filter defines a path of the emitted x-ray beam towards the x-ray receptor.

In an example, blocking a portion of an emitted x-ray beam further includes covering one aperture of a pair of apertures via at least one collimator blade of a collimator. In another example, imaging the patient's breast and imaging the one or more tissue specimens are performed under the same breast compression procedure. In yet another example, the method further includes placing the container on the support platform and within an imaging area that corresponds to the x-ray receptor disposed within the support platform. In still another example, placing the container on the support platform includes placing the container within a right anterior area of the imaging area or within a left anterior area of the imaging area. In an example, the method further includes placing the container on the compression paddle.

In another example, obtaining one or more tissue specimens includes excising the one or more tissue specimens via a vacuum assisted biopsy device and retaining the one or more tissue specimens includes capturing the one or more tissue specimens in a reservoir. In yet another example, the reservoir is independently moveable relative to the x-ray source and the x-ray receptor. In still another example, imaging the patient's breast occurs at a first focal spot size of the x-ray source and imaging the one or more tissue specimens occurs at a second focal spot size, and the first focal spot size is greater than the second focal spot size.

DETAILED DESCRIPTION

Figure 1:
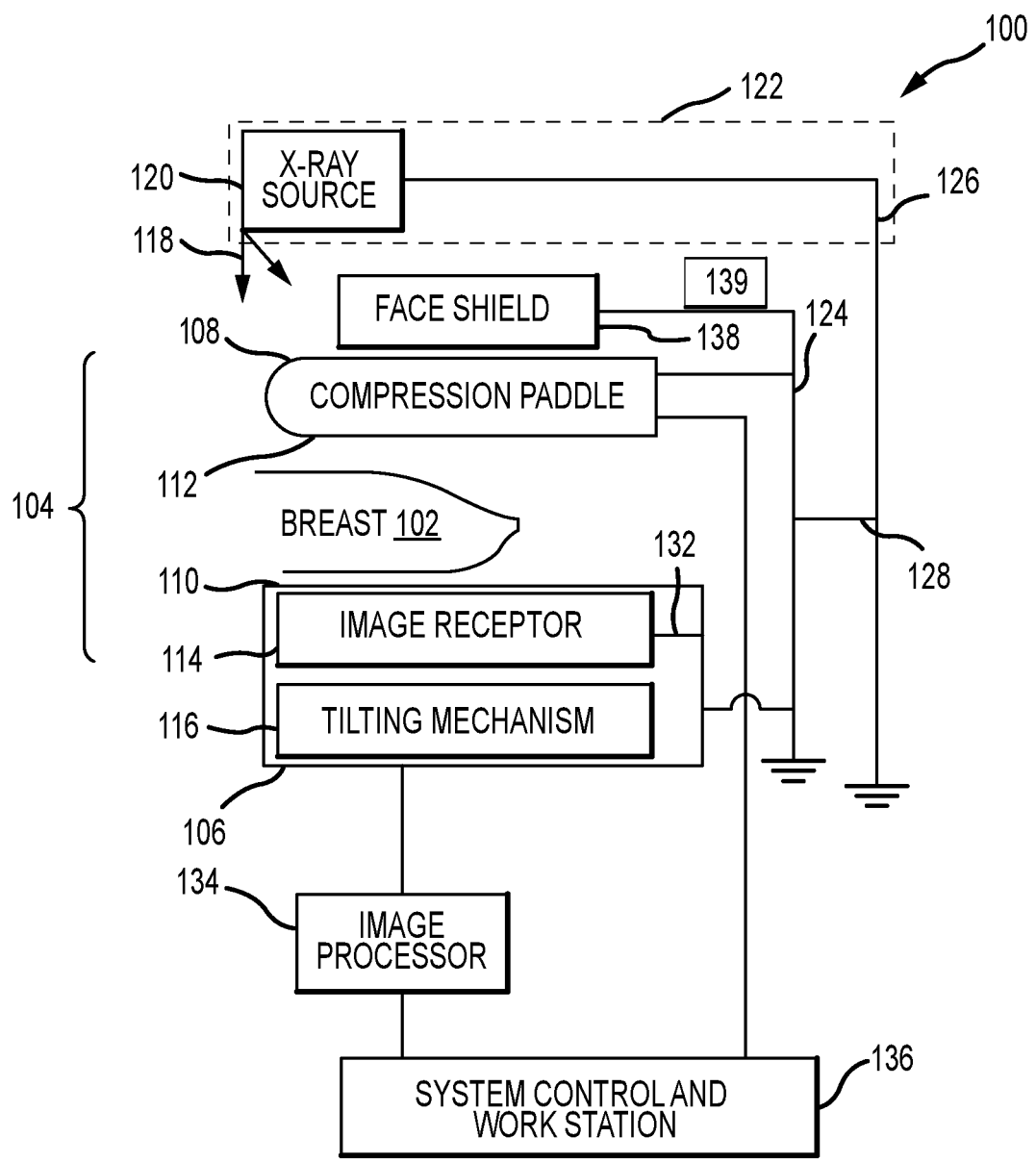
FIG. 1 is a schematic view of an exemplary imaging system.
Figure 2:
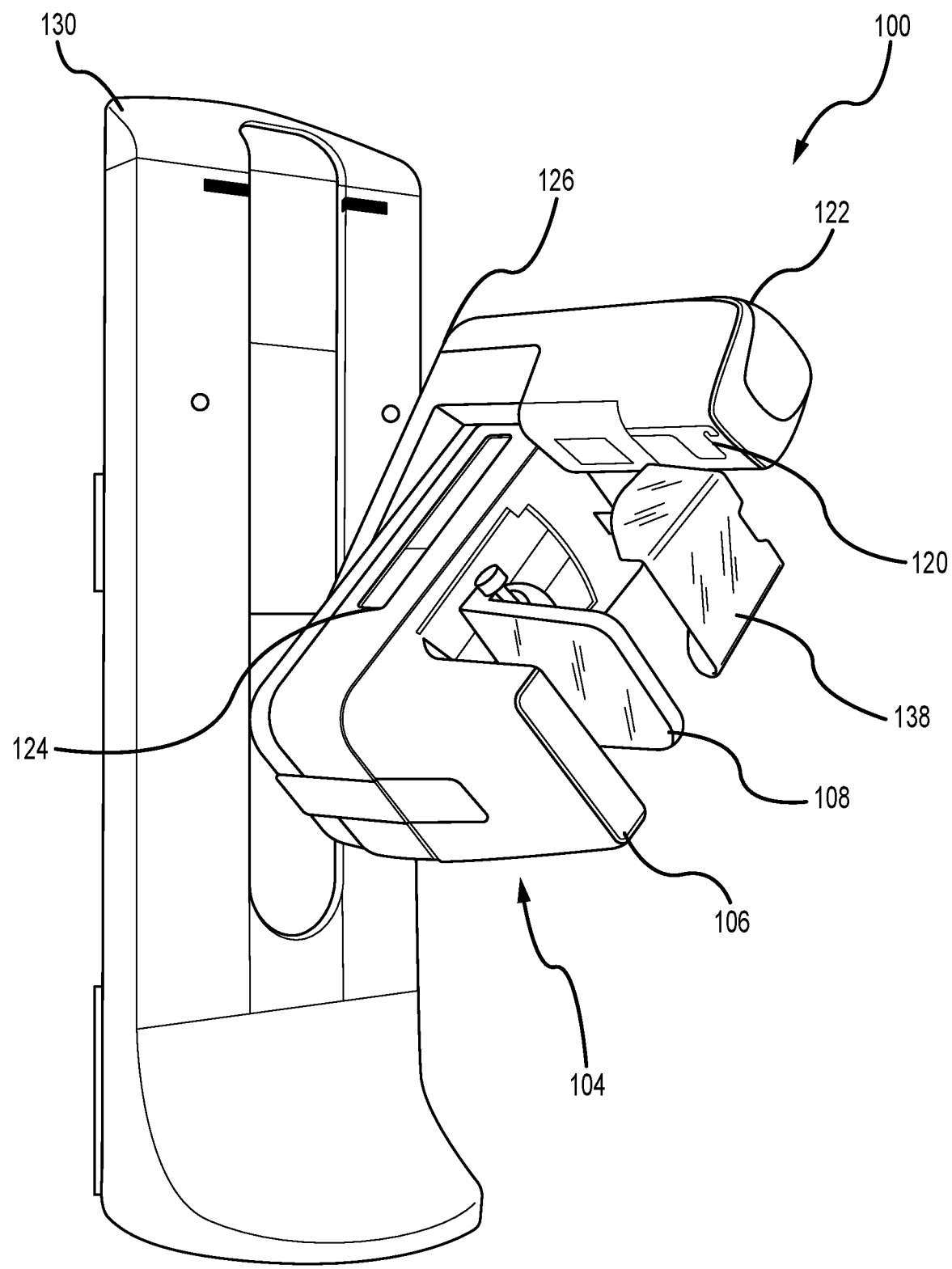
FIG. 2 is a perspective view of the imaging system of FIG. 1.

FIG. 1 is a schematic view of an exemplary imaging system 100. FIG. 2 is a perspective view of the imaging system 100. Referring concurrently to FIGS. 1 and 2, the imaging system 100 is configured to immobilize a patient's breast 102 for x-ray imaging (either or both of mammography and tomosynthesis) via a breast compression immobilizer unit or compression system 104. In the example, the compression system 104 includes a static breast support platform 106 and a moveable compression paddle 108. The breast support platform 106 and the compression paddle 108 each have a compression surface 110 and 112, respectively, with the compression surface 112 configured to move towards the support platform 106 to compress and immobilize the breast 102. In known systems, the compression surfaces 110, 112 are exposed so as to directly contact the breast 102. The support platform 106 also houses an image receptor 114 (e.g., an x-ray detector) and, optionally, a tilting mechanism 116. The immobilizer unit 104 is in a path of an imaging x-ray beam 118 emanating from an x-ray source 120 disposed within an x-ray tube head 122, such that the beam 118 impinges on the image receptor 114.

The compression system 104 is supported on a first support arm 124 and the x-ray source 120 is supported on a second support arm, also referred to as a tube arm 126. For mammography, support arms 124 and 126 can rotate as a unit about an axis 128 relative to a gantry 130 between different imaging orientations such as cranial-caudal (CC) and mediolateral oblique (MLO) views, so that the imaging system 100 can take a mammogram projection image at each orientation. In operation, the image receptor 114 remains in place relative to the support platform 106 while an image is taken. The immobilizer unit 104 releases the breast 102 for movement of support arms 124, 126 to a different imaging orientation. For tomosynthesis, the support arm 124 stays in place, with the breast 102 immobilized and remaining in place, while at least the tube arm 126 rotates the x-ray source 120 relative to the immobilizer unit 104 and the compressed breast 102 about the axis 128. The imaging system 100 takes plural tomosynthesis projection images of the breast 102 at respective angles of the x-ray beam 118 relative to the breast 102. As such, the compression system 104 and tube arm 124 may be rotated discrete from each other, unless matched rotation is required or desired for an imaging procedure.

Concurrently and optionally, the image receptor 114 may be tilted relative to the breast support platform 106 and coordinated with the rotation of the second support arm 126. The tilting can be through the same angle as the rotation of the x-ray source 120, but may also be through a different angle selected such that the x-ray beam 118 remains substantially in the same position on the image receptor 114 for each of the plural images. The tilting can be about an axis 132, which can but need not be in the image plane of the image receptor 114. The tilting mechanism 116 that is coupled to the image receptor 114 can drive the image receptor 114 in a tilting motion. For tomosynthesis imaging and/or CT imaging, the breast support platform 106 can be horizontal or can be at an angle to the horizontal, e.g., at an orientation similar to that for conventional MLO imaging in mammography. The imaging system 100 can be solely a mammography system, a CT system, or solely a tomosynthesis system, or a "combo" system that can perform multiple forms of imaging. One example of such a combo system has been offered by the assignee hereof under the trade name Selenia Dimensions.

When the system is operated, the image receptor 114 produces imaging information in response to illumination by the imaging x-ray beam 118, and supplies it to an image processor 134 for processing and generating breast x-ray images. A system control and work station unit 136 including software controls the operation of the system and interacts with the operator to receive commands and deliver information including processed-ray images. In some examples, a face shield 138 may be coupled to the support arm 124 and between the x-ray source 120 and the compression paddle 108. The face shield 138 can be used to prevent the patient from moving into the x-ray beam 118 emitted from the x-ray tube head 122 during imaging. Additionally or alternatively, a biopsy assembly 139 may be removably coupled to the support arm 124 so as to obtain tissue specimens from the patient's breast 102.

One challenge with the imaging system 100 is how to efficiently verify that the tissue specimens are obtained from the required or desired area of the breast 102 and/or to efficiently analyze the tissue specimens once imaged. In some known examples, the obtained tissue specimens are taken by the technologist to a separate and discrete specimen imaging system for this verification or analysis. By using a separate imaging system for specimen imaging, however, patient discomfort may be increased because of the increased time spent compressed at the imaging system. Additionally, increased costs are incurred by acquiring and maintaining two separate imaging systems. In other examples, the obtained tissue specimens may be imaged directly on the mammography/tomosynthesis gantry imaging system itself. In these systems, however, the specimen imaging is performed by a secondary imaging system added onto the primary imaging system, and thus, requires the technologist to switch between the two systems. That is, these systems include a primary x-ray source and receptor for mammography and tomosynthesis imaging procedures and an additional secondary x-ray source and receptor for tissue specimen imaging procedures. This is because the imaging requirements for mammography and tomosynthesis images are often different than for specimen images and the primary imaging system may not generate the resolution needed for specimen image analysis. As such, the technologist is required to place the tissue specimen outside of the primary receptor area and into the secondary receptor area, while selectively uncovering the secondary x-ray source in order to perform specimen imaging procedures. These secondary imaging systems may also increase time spent compressed at the imaging system for the patient because of the need of the technologist to switch between the two separate imaging systems. For example, for the technologist to verify that a required or desired tissue area was biopsied. Additionally, increased costs are incurred having duplicate imaging components within the gantry imaging system.

The technologies described herein relate to imaging tissue specimens directly on the x-ray gantry imaging system, and with substantially similar components as those used for mammography, tomosynthesis, and/or CT imaging procedures. By using the gantry imaging system for tissue specimen imaging, acquiring verification and/or diagnostic images is more efficient to perform. This can also help reduce patient discomfort associated with compression and the imaging process. These technologies generally improve the accuracy and resolution of the acquired tissue specimen images, enabling the technologist to more efficiently provide verification and analysis of the tissue specimen at the gantry imaging system.

As described herein, the technologies for tissue specimen imaging utilize the existing x-ray source and x-ray receptor within the gantry imaging system. This reduces costs associated with having multiple imaging systems. In one aspect, a specimen imaging filter is provided in the tube head so as to define a path of the x-ray beam towards the receptor. For example, a left or a right side of the x-ray receptor. This enables for one or more tissue specimens to be placed directly on the breast support platform for tissue specimen imaging. Additionally, the patient's breast may remain compressed during the tissue specimen imaging so that additional specimens can be obtained as required or desired. This configuration also enables for the system control and work station unit 136 to more easily automate the tissue specimen imaging process for the technologist.

In another aspect, the tissue specimens may be placed in a container that replaces the compression paddle on the image gantry. With the tissue specimen positioned between the x-ray source and the x-ray receptor, the container is configured to independently rotate relative to the compression system so that the multiple tissue specimen images at different positions may be acquired without rotating the tissue specimen itself. These positions may be for orthogonal views and/or for a CT image scan. Additionally in the examples described herein, the x-ray source may be configured for a plurality of focal spot sizes so as to enable image resolution as required or desired during the tissue specimen image acquisition as described herein.

In still another aspect, the tissue specimens may be placed directly on top of the compression paddle for tissue specimen imaging. For example, the tissue specimens can be held in a container and the container can be placed on a left, a right, or an anterior side of the compression paddle. In some examples, a specimen imaging filter may be provided in the tube head so as to define an x-ray path in relation to the placement of the tissue specimen on the compression paddle. This configuration also allows the patient's breast to remain compressed during the tissue specimen imaging and for the system control and the work station unit 136 to be used during the tissue specimen imaging process.

In yet another aspect, a vacuum assisted biopsy device can be coupled to the imaging system and used to excise a tissue specimen. For example, the excised tissue specimen is captured at a reservoir that is then used for tissue specimen imaging on the gantry. The reservoir can at least partially compress the tissue specimen and the reservoir can be coupled to the support arm so that the reservoir can move (e.g., up and/or down relative to the x-ray source, and/or rotate) and facilitate tissue specimen imaging procedures. In some examples, a specimen imaging filter may be provided in the tube head so as to define an x-ray path in relation to the placement of the reservoir and the work station unit 136 to be used during the tissue specimen imaging process.

Returning to FIG. 1, the x-ray beam 118 from the x-ray source 120 is generated by converting energy from electrons into photons within an x-ray tube having a cathode and an anode. The cathode expels electrons from an electrical circuit and focuses the electrons in a beam directed to the anode. The anode converts the energy from the electrons into x-rays and dissipates the heat generated in the process. The surface area of the anode that produces the x-rays is known as a focal spot and the dimensions of the focal spot are at least partially determined by the dimensions of the electron beam emitted from the cathode. In general, smaller focal spot sizes increase image detail, while larger focal spots enable for greater heat-dissipating capacity, but have lower resolution. Furthermore, smaller focal spots typically generate lower power x-rays than the larger focal spots. This often requires that the time period to acquire x-ray images using smaller focal spots to be greater than the time period to acquire x-ray images using larger focal spots.

The x-ray tube typically used for mammography and tomosynthesis images has two focal spot sizes. A first or normal screening size is about 300 μm (micrometer) and a second or magnification size of about 100 μm. In some examples, one or both of the first and second focal spot sizes may be sufficient to perform tissue specimen imaging as described herein and provide verification imaging to the technologist. This is because some known verification techniques only look for calcifications within the tissue specimen and high resolution visibility may not be required or desired. The systems and methods described herein enable the tissue specimen imaging to be performed directly on the gantry imaging system and use the first and/or second focal spot sizes for image acquisition.

In other examples, however, the tissue specimen image acquisition may require or desire better visibility of detail than provided by the first and second focal spot sizes. As such, the x-ray source 120 may include three or more focal spot sizes. In the example, the x-ray source 120 also has a third or micro focal spot size of less than or equal to 50 µm. In an aspect, the third micro focal spot size enables a geometric magnification factor of about 1.8 or higher to be achieved by the x-ray source 120. By using a third micro focal spot size, the x-ray source 120 can acquire tissue specimen images with increased detail as tissue specimens are generally smaller, by orders of magnitude, than the patient's breast. For example, core tissue specimens are about 2.5 mm (millimeters) thick, while lumpectomy tissue specimens are about 5 cm (centimeters) thick. A single x-ray tube of the x-ray source 120 may enable for the three different focal spot sizes to be formed on the anode. In other examples, two or more x-ray tubes may be used at the x-ray source 120 so as to enable the three different focal spot sizes.

Furthermore, by using the third micro focal spot size, not only is imaging detail increased so as to increase verification efficiency of the technologist, but diagnostic image analysis can be performed as required or desired. This further reduces the need for a separate tissue specimen imaging system as the imaging system 100 can be used for all of the tissue specimen imaging needs as required or desired. While the third micro focal spot size could be used for mammography and/or tomosynthesis image acquisition, this configuration is typically not used for these imaging modes because the power of the x-rays is reduced, thereby increasing the time period that the patient is immobilized so as to not blur the x-ray image. The exposure time period for tissue specimens, however, is not as important because the specimens do not actively move.

In the example, each of the three focal spot sizes of the x-ray source 120 can be used with the x-ray receptor 114 disposed within the support platform 106. While the image area of the larger focal spot sizes may be slightly larger than the smaller focal spot sizes (e.g., because of the size of the electron beam), this difference is negligible during image acquisition and the general location of the image area remains substantially similar with respect to the x-ray receptor 114 for all three focal spot sizes.

Figure 4:
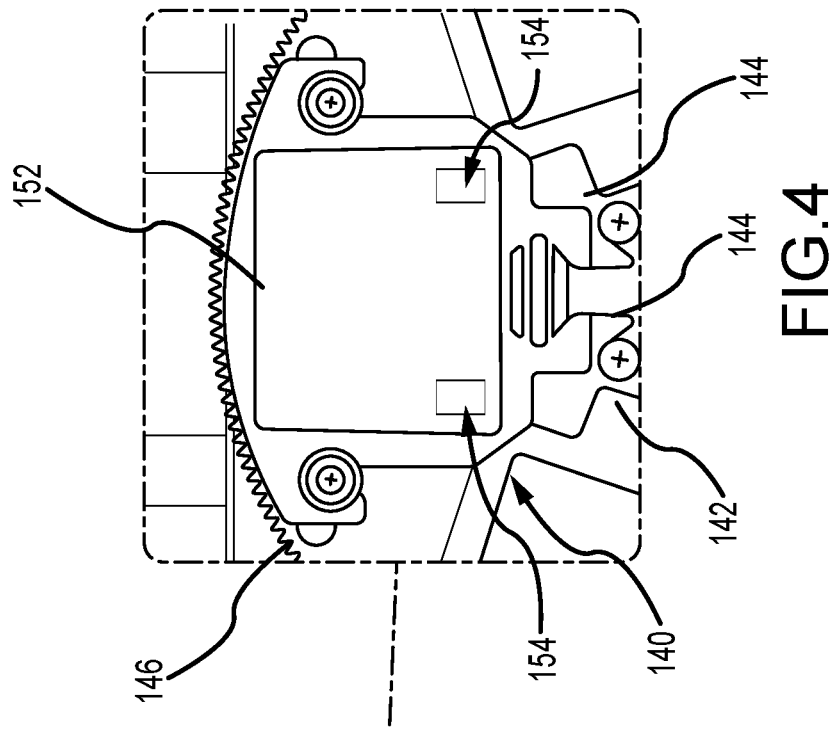
FIG. 4 is an enlarged view of a portion of a filter wheel assembly of the x-ray tube head shown in FIG. 3.
Figure 3:
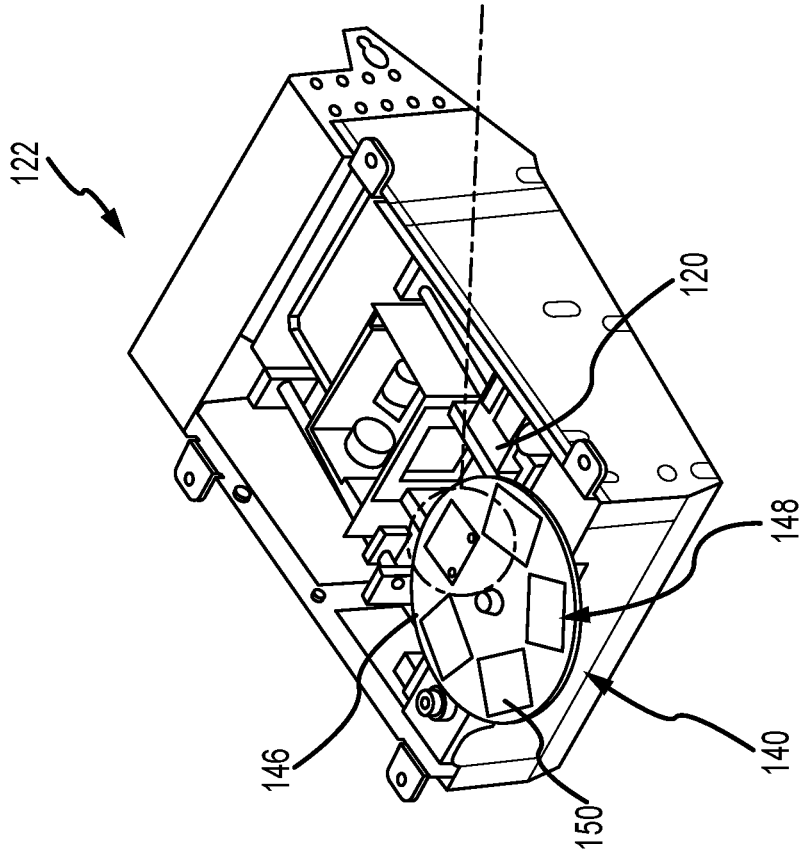
FIG. 3 is a partial internal perspective view of an x-ray tube head.

FIG. 3 is a partial internal perspective view of the x-ray tube head 122. FIG. 4 is an enlarged view of a portion of a filter wheel assembly 140 of the x-ray tube head 122 (shown in FIG. 3). Referring concurrently to FIGS. 3 and 4, the x-ray tube head 122 houses the x-ray source 120 that generates the x-ray beam 118 (shown in FIG. 1) for acquiring x-ray images. The x-ray tube head 122 also tilts (e.g., ±15°) relative to the breast support platform 106 (shown in FIG. 2). The x-ray tube head 122 also includes a collimator 142 and the filter wheel assembly 140, both positioned adjacent the x-ray source 120. The collimator 142 includes one or more blades 144 that are configured to move at least partially within the emitted x-ray beam. The blades 144 filter the x-ray beam so that the x-rays that pass through the collimator 142 are aligned in a specific direction. For example, the collimator blades 144 are configured to define a path of the emitted x-ray beam in a direction towards the x-ray receptor 114 (shown in FIG. 1).

The filter wheel assembly 140 includes a filter wheel 146 having a plurality of filter slots 148. Each of the filter slots 148 is configured to receive a filter 150. The filter wheel 146 is rotatable so that the filter slots 148 are selectively positionable within the emitted x-ray beam. The filter wheel assembly 140 is downstream (relative to the emitted x-ray beam direction) from the x-ray source 120 and the collimator 142. The filters 150 can be any filter that enables operation of the imaging system 100 as described herein. For example, one of the filters 150 can be a copper filter that filters high-energy x-rays for high-energy image acquisitions. Other examples of filters are silver or aluminum filters, or full lead filters so as to enable testing of the imaging system. In another example, the filters 150 are between approximately 2 and 3 thousandth of an inch (mils). In an aspect, the filters 150 are approximately 2.35 mils. As illustrated in FIG. 3, the filter wheel 146 includes five filter slots 148, however, the filter wheel 146 may include any other number of slots 148 as required or desired. For example, the filter wheel 146 may include four filter slots 148.

In the example, a specimen imaging filter 152 is disposed within at least one slot 148 of the filter wheel 146. The specimen imaging filter 152 is configured to enable the x-ray source to acquire tissue specimen images as described herein. The specimen imaging filter 152 includes at least one aperture 154 defined therein, and is selectively positionable within the emitted x-ray beam (via the filter wheel 146) so as to block a portion of the emitted x-ray beam and allow the aperture 154 to define a path of the emitted x-ray beam to the x-ray receptor. In an aspect, the specimen imaging filter 152 is formed from lead material so as to block the emitted x-rays except for the aperture 154. In another aspect, the filters 152 is approximately 2.35 mils. In other examples, the specimen imaging filter 152 can be formed from any other material that enables the filter to function as described herein.

The at least one aperture 154 can include a pair of apertures that are sized and shaped to define the path of x-rays to a predetermined focus area on the support platform. In one example, the apertures 154 may be substantially rectangular-shaped. For example, the short edge of the rectangle can be disposed proximate the back of the filter as illustrated, or the long edge of the rectangle can be disposed proximate the back of the filter (not illustrated). In other examples, the apertures 154, may be triangular-shaped, square-shaped, circular-shaped, or any other shape that enables the specimen imaging filter 152 to function as described herein. In the example, the pair of apertures 154 are both disposed at one end of the filter 152 and on opposite left and right sides. This position of the apertures 154 enables the specimen imaging filter 152 to define a path of the emitted x-ray beam that is directed to a right or a left anterior area of the x-ray receptor so as to image tissue specimens with the same x-ray source and receptor that are used for mammography and tomosynthesis images as described above. The collimator blades 144 can be used to selectively cover one of the apertures 154 so that only one aperture 154 (e.g., the left or the right) is used during tissue specimen imaging procedures. The right and left anterior areas are described further below in reference to FIG. 5.

Additionally, the x-ray tube head 122 can tilt (e.g., to the right or the left) during the tissue specimen imaging procedures. For example, to image the right anterior area, the x-ray tube head 122 can tilt to the right. Conversely, to image the left anterior area, the x-ray tube head 122 can tilt to the left. This movement can assist in defining the path of x-rays to the specific area on the support platform and reduce or prevent imaging other components. In another aspect, the x-ray tube head 122 tilts to the opposite side of the collimator blade 114 that covers one of the apertures 154. For example, when the collimator blade 144 covers the left aperture, the x-ray tube head 122 tilts to the right and towards the side of the uncovered right aperture. In an aspect, during the tissue specimen imaging procedures, the x-ray tube head 122 can tilt about ±15° to the left and right.

In other aspects, the tilting to the left or right of the x-ray tube head 122 can be less than 15°, or greater than 15°, as required or desired.

In other examples, the at least one aperture 154 can be positioned within the specimen imaging filter 152 to define a path of the emitted x-ray beam that is directed towards specific locations on the compression paddle (e.g., left edge, right edge, or anterior location). These locations are described further below in reference to FIGS. 10-12, but still enable imaging of the tissue specimen with the same x-ray source and receptor that are used for mammography and tomosynthesis images as described above. In another example, the at least one aperture 154 can be positioned within the specimen imaging filter 152 to define a path of the emitted x-ray beam that is directed to a specific location of a vacuum assisted biopsy device as described further below in reference to FIGS. 13-15. This also still enables imaging of the tissue specimen with the same x-ray source and receptor that are used for mammography and tomosynthesis images as described above.

In the example, the specimen imaging filter 152 can be used with any focal spot size generated by the x-ray source 120. This enables for the tissue specimen to be imaged in any amount of detail as required or desired. For example, using a focal spot size for verification procedures (e.g., a larger focal spot size) or for verification and diagnostic procedures (e.g., a smaller focal spot size).

Figure 5:
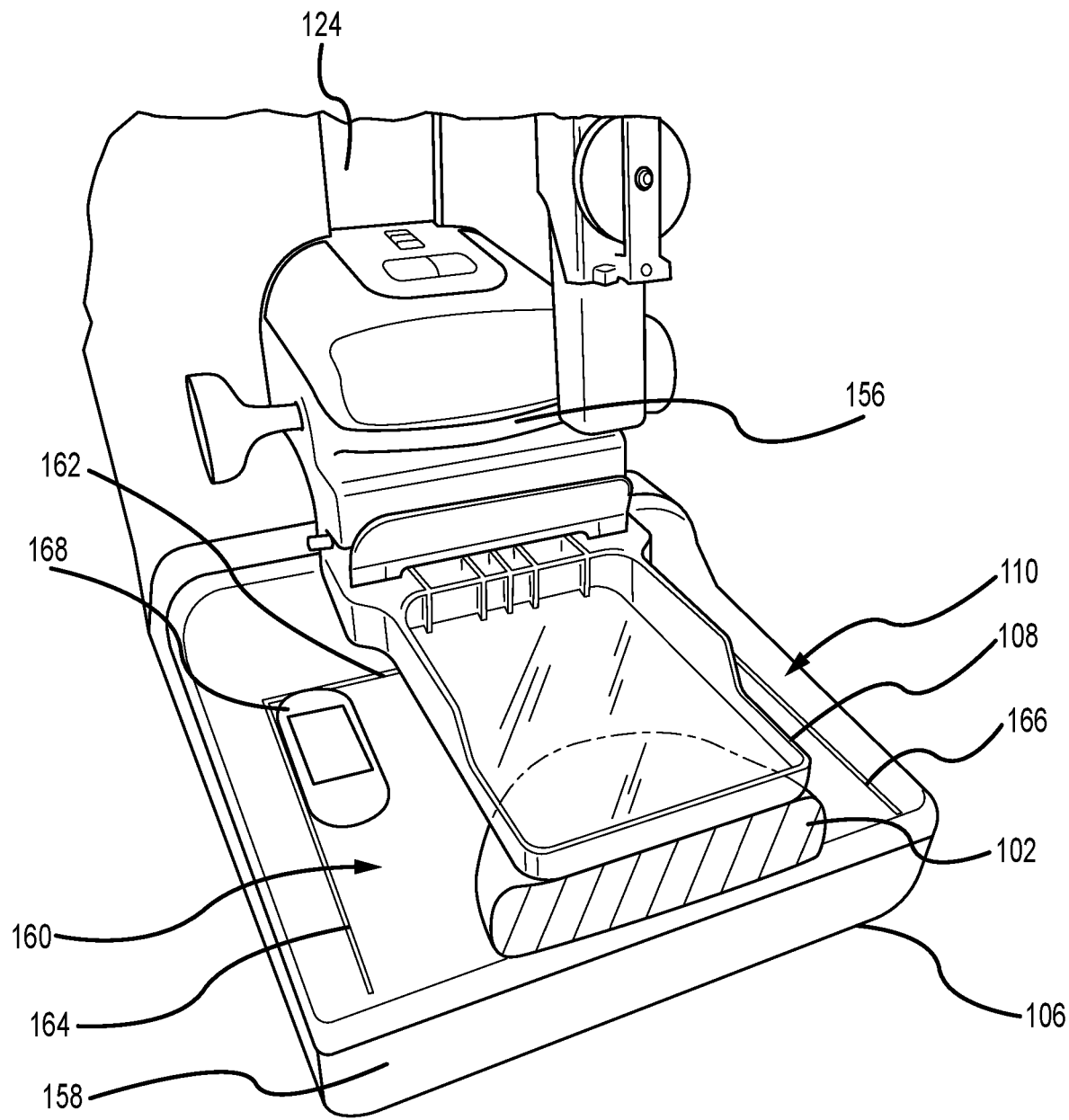
FIG. 5 is a perspective view of a support platform of the imaging system shown in FIGS. 1 and 2.

FIG. 5 is a perspective view of the support platform 106 of the imaging system 100 (shown in FIGS. 1 and 2). As described above, the support platform 106 extends from the support arm 124 that also supports the compression paddle 108. The support platform 106 houses the x-ray receptor 114 (shown in FIG. 1) that enables x-ray images to be acquired. The compression surface 110 of the support platform 106 is used to compress the patient's breast 102 (represented in FIG. 5 by a breast phantom) with the compression paddle 108. The compression paddle 108 is coupled to the support arm 124 with a paddle bracket 156 that is configured to move (e.g., in an up and down direction) relative to the support platform 106 and along the support arm 124.

In operation, the patient's breast 102 is compressed between the support platform 106 and compression paddle 108 while one or more imaging procedures are performed (e.g., mammography and/or tomosynthesis). The patient's chest wall is typically positioned against a front wall 158 of the support platform 106 so as to enable breast compression. These images are acquired via the x-ray receptor 114 that is disposed within the platform 106. In the example, the x-ray receptor 114 at least partially defines an imaging area 160 (e.g., the relative size of the receptor) that enables the patient's breast 102 to be imaged. Because the x-ray receptor is below the compression surface 110, the imaging area 160 can be visually identified for the technologist by a box on the compression surface 110. In other examples, the imaging area 160 can be identified by any other indicator(s) as required or desired. For example, the imaging area 160 can be identified by pixel markers on the x-ray receptor. The imaging area 160 extends from the front wall 158 of the support platform 106 towards an anterior portion 162 of the compression surface 110 that is proximate the support arm 124. Additionally, the imaging area 160 includes left and right portions 164, 166, respectively.

Additionally or alternatively, the patient's breast 102 may be compressed for a biopsy procedure to be performed (e.g., via a biopsy assembly that is not illustrated) so as to obtain one or more tissue specimens from the patient's breast 102. These biopsied tissue specimens can then be imaged by the imaging system 100. The tissue specimen imaging can be for verification (e.g., that the area of interest was biopsied), diagnostics, and/or any other procedure as required or desired. In order to increase the efficiency of the tissue specimen imaging process and to decrease patient discomfort (e.g., from long time periods of breast compression), the same imaging components of the imaging system 100 for mammography and tomosynthesis imaging are used.

In the example, after biopsy, the technologist can place and retain the tissue specimens in a specimen container 168. The specimen container 168 can be a radiolucent container that is configured to retain tissue specimens and enable the tissue specimens to be moved by the technologist. In an aspect, the specimen container 168 is configured to be positioned within the imaging area 160 and lay flat on the support platform 106. In some examples, the specimen container 168 may be disposable, for example, such as those produced by Faxitron Bioptics. Additionally or alternatively, the specimen container 168 can hold a plurality of tissue specimens; for example, at least four to six separate specimens. The plurality of tissue specimens can be separated into discrete compartments within the specimen container 168 or all within a single large compartment.

As illustrated in FIG. 5, the size and shape of the specimen container 168 allows for the container to be placed within the imaging area 160 and offset from the compression paddle 108 so that the patient's breast 102 can remain compressed during tissue specimen imaging. For example, the specimen container 168 can be placed in a left anterior area (e.g., towards the corner of the anterior portion 162 and the left portion 164) and/or a right anterior area (e.g., towards the corner of the anterior portion 162 and the right portion 166). In an aspect, pixel markers can be used for the placement of the specimen container 168. For example, markers for pixel location can be placed on rear anterior line and edges on each sides (e.g., 0 pixel line). This offset positioning relative to a centerline of the x-ray receptor 114 also corresponds with the structure (e.g., the apertures) of the specimen imaging filter 152 described above in reference to FIGS. 3 and 4 so that the path of the x-ray beam is directed to the tissue specimens retained within the specimen container 168 and positioned within the imaging area 160. Furthermore, this process for tissue specimen imaging is performed on the gantry within the imaging area 160 of the x-ray receptor 114 and duplicate imaging components are not needed. In some examples, the focal spot size of the x-ray source can be adjusted as required for verification or diagnostic imagining. Additionally, the x-ray tube head can tilt towards the left or right imaging area as required or desired.

Figure 6:
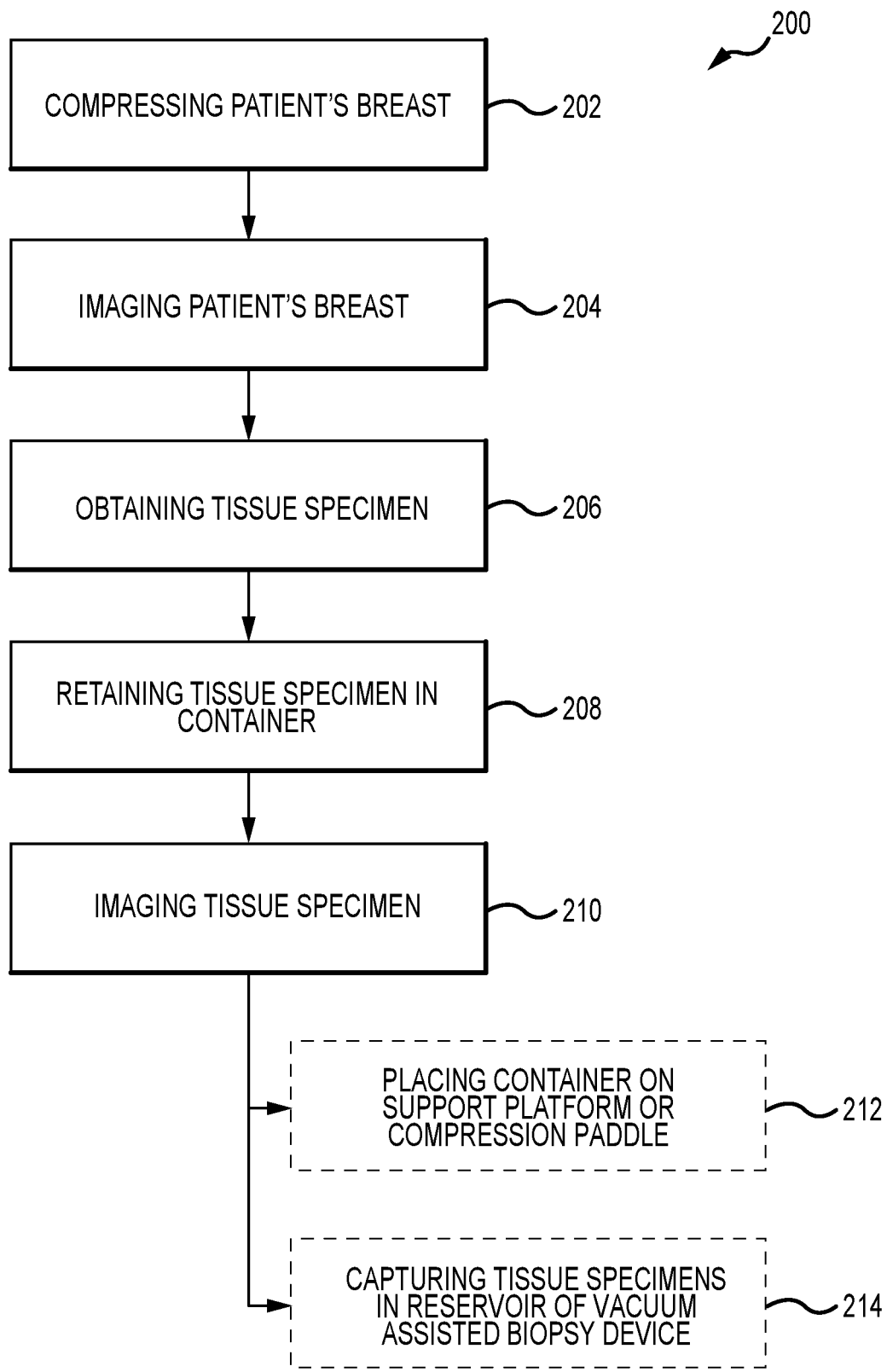
FIG. 6 depicts a flowchart illustrating a method of acquiring a tissue specimen image.

FIG. 6 depicts a flowchart illustrating a method 200 of acquiring a tissue specimen image on an x-ray breast imaging system. The imaging system is configured to acquire x-ray images (e.g., mammography, tomosynthesis, and/or CT images) and can be the imaging system described above in FIGS. 1-5. The method 200 begins with compressing a patient's breast between a compression paddle and a support platform (operation 202). Once compressed, the patient's breast can be imaged via an x-ray source disposed in an x-ray tube head and an x-ray receptor disposed in the support platform (operation 204). This breast imaging procedure can be performed under any number of imaging modes and include any number of different images. For example, mammography images such as CC and/or MLO views, tomosynthesis scanning that includes a plurality of projection images, CT imaging, stereotactic imaging, contrast imaging, or any other imaging procedure as required or desired.

While the patient's breast is immobilized, one or more tissue specimens are obtained from the patient's breast (operation 206). In one example, the tissue specimens may be obtained from a biopsy procedure, and for example, by a biopsy assembly that attaches to the imaging system and controllable by the work station unit. In another example, the tissue specimens may be obtained using a handheld biopsy device operable by the technologist. The tissue specimens obtained can be of any type as required or desired. For example, core tissue specimens, mastectomy tissue specimens, and/or lumpectomy tissue specimens. In another example, during the biopsy procedure one or more x-ray images may be acquired. For example, by a stereotactic biopsy procedure for needle location verification. The specimen imaging process as described herein can be an alternative to, or in addition to, post-clip x-ray imaging. Once the tissue specimens are obtained, the technologist can retain the tissue specimens in a container (operation 208). The container is configured to hold the tissue specimens for one or more subsequent procedures. For example, the container may be configured to support the tissue specimens for imaging on the gantry imaging system. Additionally or alternatively, the container may be configured to store the tissue specimens for transportation to a pathology lab.

The method 200 then includes imaging the tissue specimens via the same x-ray source used for imaging the patient's breast (operation 210). In the example, the same x-ray receptor that is disposed within the support platform is also used for both of the breast imaging and the tissue specimen imaging. This tissue specimen imaging can include verification imaging so as to enable the technologist to verify that the tissue specimen was obtained from the correct area. Additionally or alternatively, the this tissue specimen imaging can include diagnostic imaging with a higher image resolution from a micro focal spot size as described above in reference to FIGS. 1 and 2. For example, the imaging of the patient's breast (operation 204) can occur at a first focal spot size of the x-ray source and the imaging of the tissue specimens can occur at a second focal spot size of the x-ray source, and the first focal spot size is greater than the second focal spot size.

Once the tissue specimens are placed on or within the imaging area, imaging the tissue specimens (operation 210) may include selectively blocking a portion of an emitted x-ray beam from the x-ray source. By blocking a portion of the emitted x-ray beam, a path of the x-ray beam can be defined specifically towards the location of the tissue specimen that is placed on the support platform or within the x-ray field. In one example that is described herein, a specimen imaging filter with at least one aperture can be used block some of the x-rays and define the path of the x-ray beam towards the x-ray receptor. In this example, the specimen imaging filter can include a pair of apertures and one of the apertures are covered by one or more collimator blades so as to block at least a portion of the x-ray beam. As such, depending on the left or right area that the tissue specimen is placed, the collimator blade can selectively cover the opposite left or right aperture of the specimen imaging filter. These operations can be performed automatically by the work station unit (e.g., detecting the position of the tissue specimen and covering one of the apertures).

Imaging the tissue specimens (operation 210) can also include articulating the tube head to the left or right based on where the specimen container is positioned. For example, the tube head tilts to the left, when the specimen container is position on the left, and tilts to the right, when the specimen container is position on the right. In the examples that include covering one or more apertures by one or more collimator blades, the method 200 can include articulating the tube head and selectively covering or closing an aperture with a collimator blade. For example, moving the collimator blade to close the aperture for the side that the tube head does not articulate towards (e.g., closing the left aperture when the tube head tilts to the right).

Additionally, the technologist can use one or more specific imaging modality/programs on the work station unit for specimen imaging that can control the energy and dose for imaging the specimen. For example, the doses for imagining the specimen can be lower than imaging breast tissue. Additionally or alternatively, the imaging modality/programs can also be configured to allow for dual energy contrast-enhanced imaging of the specimen.

In some examples, this tissue specimen imaging can occur while the biopsy needle is still inserted into the patient's breast so that if further tissue specimens are required or desired, the patient's breast does not have to be re-compressed. In another example, imaging the patient's breast (operation 204) and imaging the tissue specimen (operation 210) is performed under the same breast compression procedure. By acquiring tissue specimen images directly on the gantry imaging system, a single system can be used for multiple imaging modes. This increases efficiency for the technologist, while decreasing patient discomfort and procedure time.

The method 200 may also include that prior to imaging the tissue specimens (operation 210), the container is placed on the support platform and within an imaging area that corresponds to an x-ray receptor disposed within the support platform (operation 212). The container may be placed within the imaging area and towards a right anterior area or a left anterior area. By placing the container in these specific areas, the tissue specimen imaging is acquired by the x-ray receptor that is within the support platform and is that is also utilized for other imaging modes. Additionally, these areas are locations on the imaging area that are out of the way of the compression paddle and the compressed breast, and typically do not have any obstructions which may produce undesirable image artifacts. For example, these areas are positioned away from the biopsy equipment and away from the front wall of the support platform that is positioned against the chest wall of the patient. Also, the path of the x-ray beams can be directed away from the patient and lower x-ray doses.

In other examples, the container may be place on top of the compression paddle (operation 212) as described further below in reference to FIGS. 10-12. In another example, retaining the tissue specimens in a container (operation 208) may include capturing the tissue specimens in a reservoir of a vacuum assisted biopsy device (operation 214) and as described further below in reference to FIGS. 13-15. Once the tissue specimen is captured in the reservoir, the reservoir may at least partially compress the tissue specimen so that the reservoir can be selectively positioned within the x-ray path because the reservoir is independently moveable relative to the x-ray source and the x-ray receptor. The tissue specimen can then be imaged via the same x-ray source used for imaging the patient's breast (operation 210).

Figure 7:
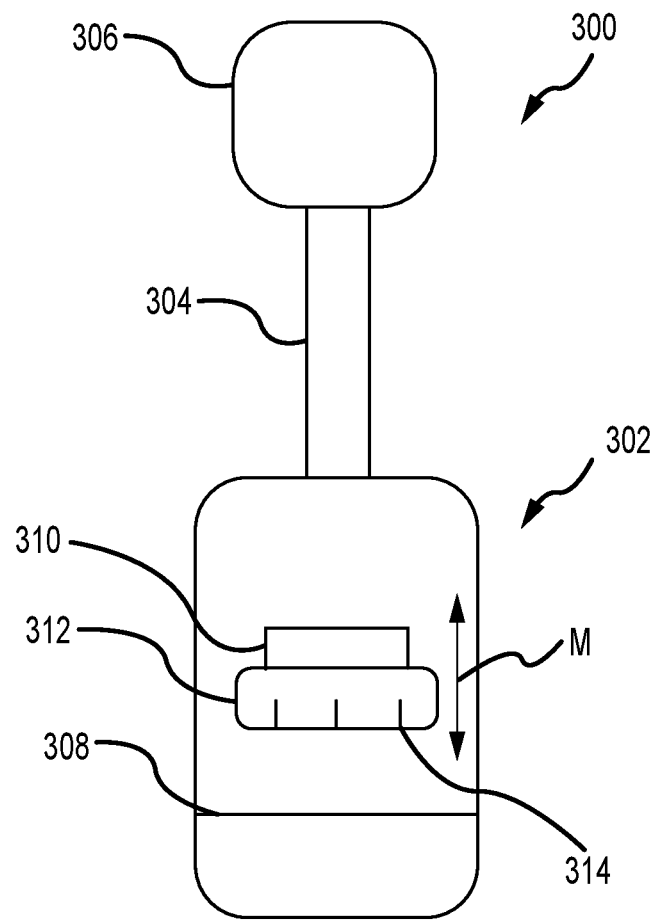
FIG. 7 is a front view of another imaging system in a first position.
Figure 8:
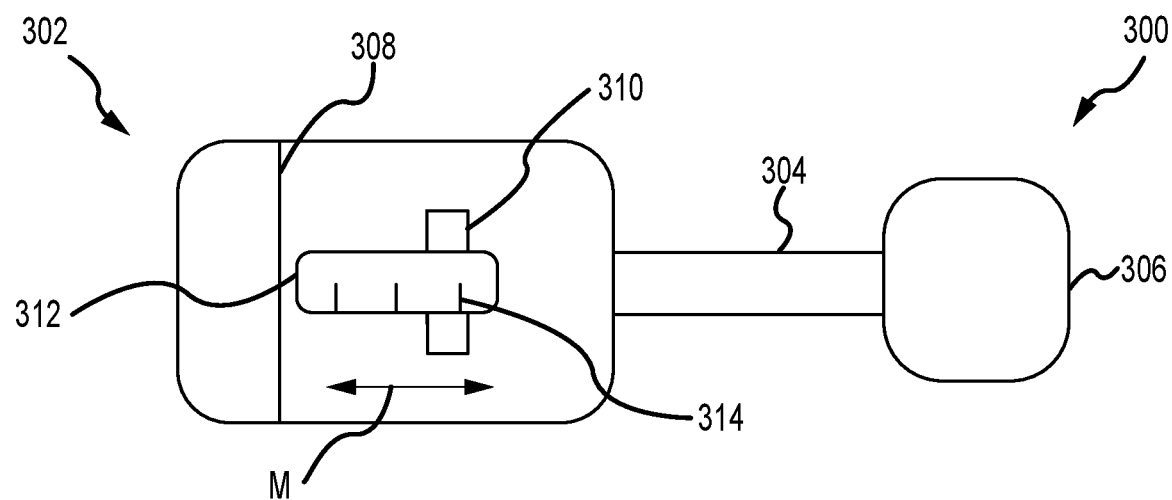
FIG. 8 is a front view of the imaging system shown in FIG. 7 in a second position.

FIG. 7 is a front view of another imaging system 300 in a first position. FIG. 8 is a front view of the imaging system 300 in a second position. Referring concurrently to FIGS. 7 and 8, the imaging system 300 is configured to acquire mammography images, tomosynthesis images, and/or CT images of a patient's breast and as described herein. The imaging system 300 includes a compression system 302, a support arm 304, and an x-ray tube head 306 that are supported by a gantry (not shown). The compression system 302 includes a support platform 308 that houses an x-ray receptor (not shown) and a paddle bracket 310 (e.g., a paddle clamp) that is movable M relative to the support platform 308. The paddle bracket 310 is configured to removably couple a compression paddle (not shown) to the compression system 302 so that a patient's breast may be compressed between the paddle and the support platform 308. The compression system 302 is coupled to the support arm 304, and in some examples, may be independently rotatably relative to the x-ray tube head 306 (e.g., for tomosynthesis imaging). An x-ray source (not shown) is disposed within the x-ray tube head 306 and is configured to generate an x-ray beam in a direction towards the x-ray receptor. In an example, the x-ray tube head 306 may include the filter wheel assembly 140 and the specimen imaging filter 152 described above in FIGS. 3 and 4 so as to increase tissue specimen imaging performance.

In this example, a specimen container 312 is configured to retain one or more tissue specimens and is removably coupleable to the compression system 302 at the paddle bracket 310. The specimen container 312 includes a mount (e.g., the component that couples to the paddle bracket 310) that enables the container 312 to remain in an upright position when the compression system 302 rotates relative to the gantry. In one example, the mount can include a powered rotating mechanism to auto-rotate the specimen container 312 during rotation of the compression system 302. The power for the rotating mechanism can be provided by the gantry, for example by the biopsy power connector location.

By allowing the specimen container 312 to remain upright, the tissue specimens contained therein do not move within the container 312 and multiple image views can be acquired at different angles. As illustrated in FIG. 7, the compression system 302 and the tube head 306 are oriented in a substantially vertical direction. In this orientation, the specimen container 312 is substantially parallel to the support platform 308 and the x-ray receptor disposed therein. When the compression system 302 and the tube head 306 are rotated to the right about 90° and are oriented in a substantially horizontal direction as illustrated in FIG. 8, the specimen container 312 via its mount rotates independently from the compression system 302 so that it remains upright and is now substantially orthogonal to the support platform 308. Although FIG. 8 illustrates rotation of the imaging system 300 to the right, it should be appreciated that the imaging system 300 can also rotate to the left and any intermediate position therebetween.

Because the x-ray imaging components (e.g., the x-ray source and receptor) can rotate relative to the tissue specimens retained within the specimen container 312, the imaging system can be utilized to perform CT imaging of the tissue specimens. Additionally, in any position of the imaging system 300 the specimen container 312 can be moved M between the x-ray source and the x-ray receptor. This allows for magnification imaging of the tissue specimen to easily occur by moving M the specimen container 312 closer to the x-ray source. The filter assembly (described above in reference to FIGS. 3 and 4) can be used to filter tissue specimen imaging as required or desired. Additionally or alternatively, the x-ray source can include two, three, or more focal spot sizes as described herein to increase resolution of the tissue specimen images.

The specimen container 312 can be any container that enables tissue specimen images to be acquired as described herein. For example, a general container that can hold one or more tissue specimens. In other examples, a specialized container can be used to hold multiple biopsy core specimens, lumpectomy specimens, and/or mastectomy specimens. These specialized containers can be sized and shaped so as to increase x-ray image efficiency during image acquisition. The specimen container 312 can include one or more radiopaque markers 314, for example, a grid to make tissue specimen imaging more efficient to analyze (e.g., measure). In sill other examples, a compression paddle may be configured to support one or more removable specimen containers (e.g., container 168 shown in FIG. 5) and have a mount that enable rotation of the container relative to other components. In yet another example, the mount may directly support one or more removable specimen containers itself. By using removable specimen containers, the tissue specimens can be more easily moved around by the technologist (e.g., transported to pathology).

In another aspect, the specimen container 312 can include a paddle identification number that is readable by the imaging system 300. The paddle identification number can be based at least partially on the tissue specimen (e.g., biopsy core, lumpectomy, mastectomies, etc.) so that tissue image acquisition can be more automated by the work station unit. This enables the specimen container 312 to be automatically positioned relative to the x-ray tube head for specific tissue specimens. In another example, the paddle identification can be used to automatically determine collimation of the x-ray beam, focal spot size, and/or filter properties of the x-ray tube head 306.

Figure 9:
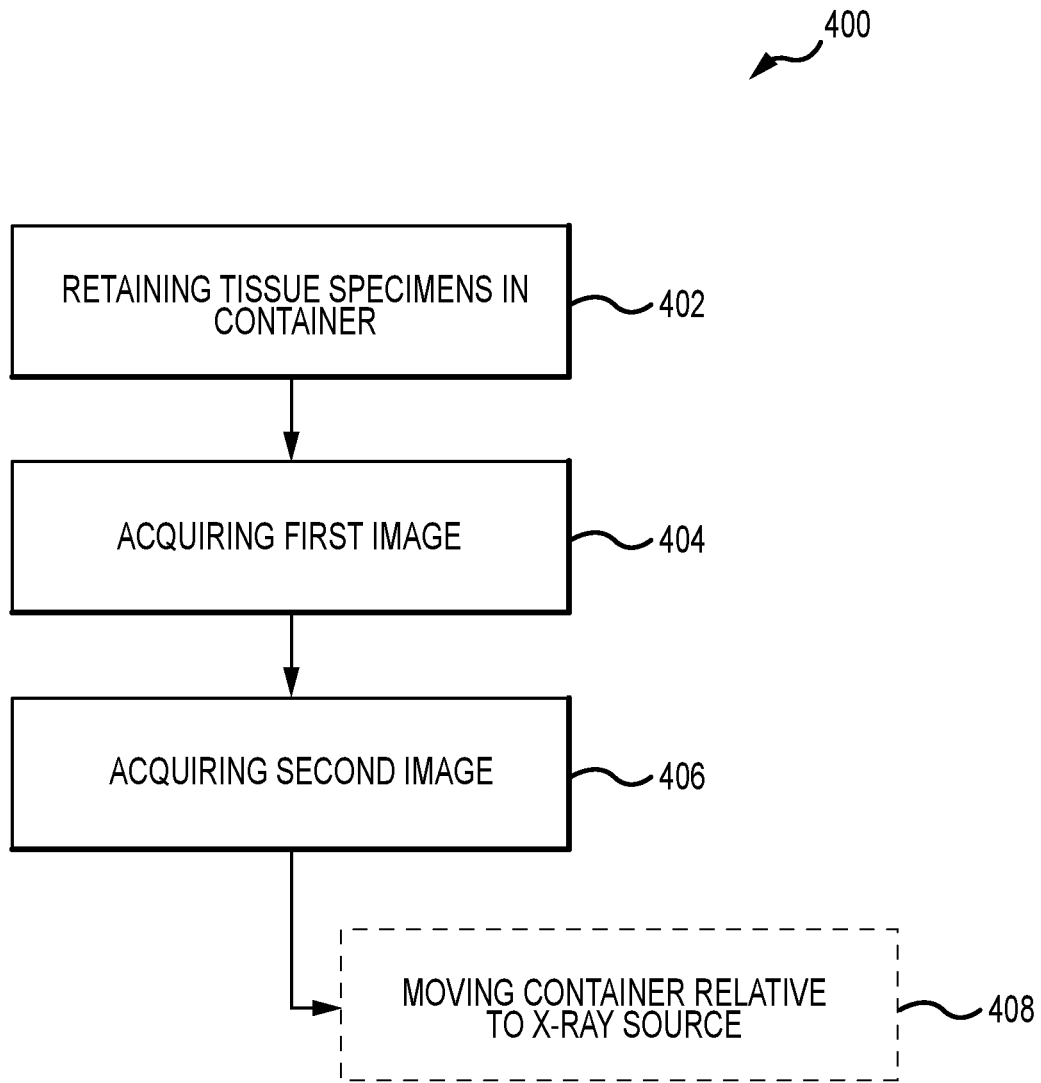
FIG. 9 depicts a flowchart illustrating a method of imaging a tissue specimen.

FIG. 9 depicts a flowchart illustrating a method 400 of imaging a tissue specimen on an x-ray breast imaging system. The imaging system is configured to acquire x-ray images (e.g., mammography, tomosynthesis, and/or CT images) and can be the imaging system described above in FIGS. 7 and 8. The method 400 begins with retaining one or more tissue specimens in a container coupled to a paddle bracket (operation 402). The tissue specimens obtained can be of any type as required or desired. For example, core tissue specimens, mastectomy tissue specimens, and/or lumpectomy tissue specimens.

Once the tissue specimens are supported by imaging system, a first image is acquired by an x-ray source and an x-ray receptor that are in a first position relative to the container (operation 404). A second image is also acquired by the x-ray source and the x-ray receptor that are in a second positon relative to the container (operation 406). The container is independently rotatable relative to x-ray source and the x-ray receptor, and the container maintains position relative to the imaging system in both the first position and the second position. As such, the tissue specimen is not required to move for the tissue imaging procedure. These imaging procedures can include a CT image scan or part of orthogonal tissue specimen views.

The method 400 may also include moving the container, via the paddle bracket, relative to the x-ray source (operation 408). This movement is typically in a direction that is substantially orthogonal to the x-ray receptor and enables magnification of the x-ray image.

Figure 10:
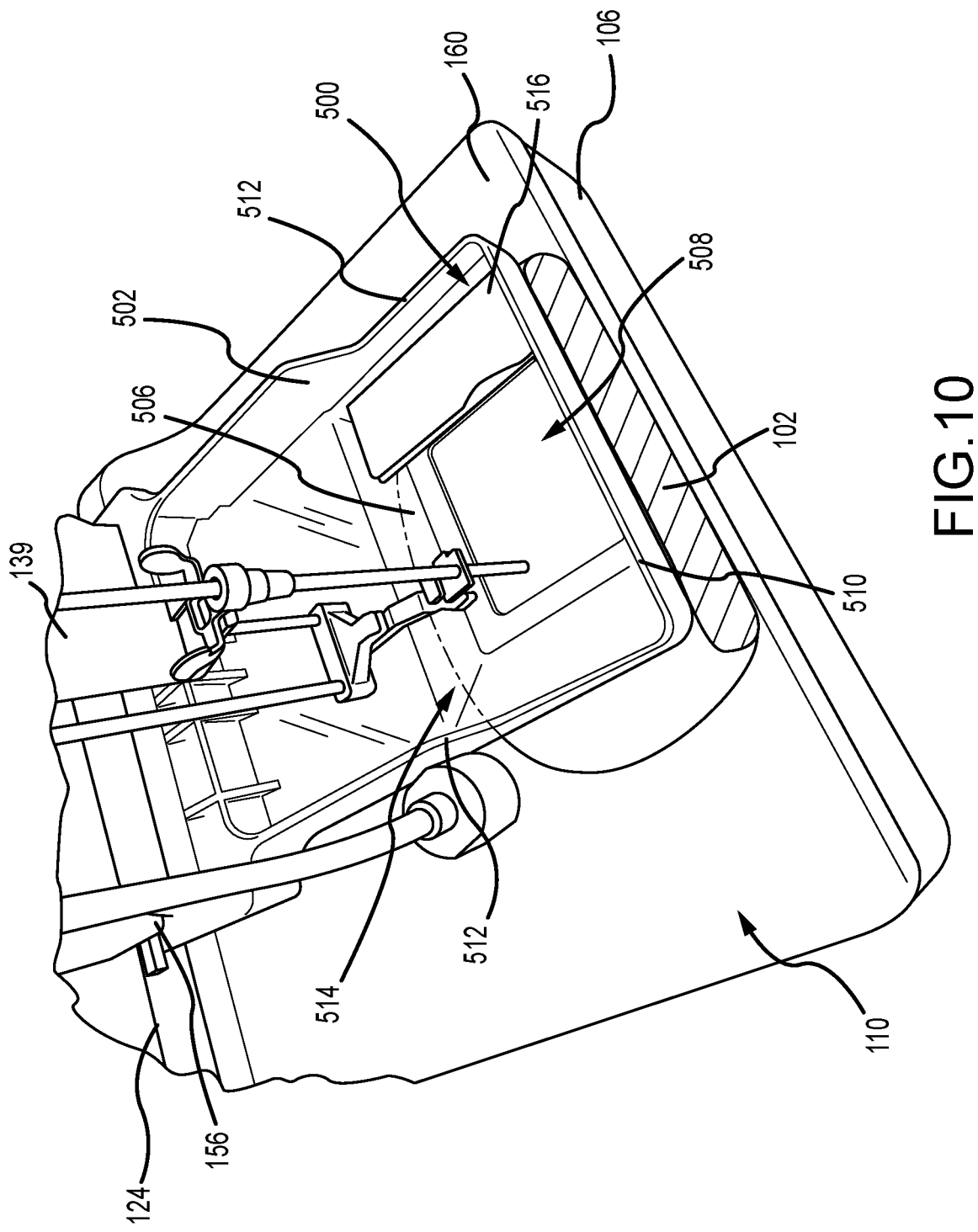
FIG. 10 is a perspective view of the support platform of the imaging system shown in FIGS. 1 and 2 with a tissue specimen within a specimen container disposed on a compression paddle.

FIG. 10 is a perspective view of the support platform 106 of the imaging system 100 (shown in FIGS. 1 and 2) with a tissue specimen 500 within a specimen container 516 disposed on a compression paddle 502. FIG. 11 is a perspective view of the support platform 106 with the tissue specimen 500 within the specimen container 516 disposed on another compression paddle 504. FIG. 12 is a perspective view of the tissue specimen 500 within the specimen container 516. Referring concurrently to FIGS. 10-12, the support platform 106 extends from the support arm 124 that also supports the compression paddle 502, 504. The compression surface 110 of the support platform 106 is used to compress the patient's breast 102 with the compression paddle 502, 504. The paddle bracket 156 can releasably couple the compression paddle 502, 504 to the support arm 124 and enable the compression paddle to move (e.g., up and down) relative to the support platform 106 so as to compress the patient's breast 102.

Figure 11:
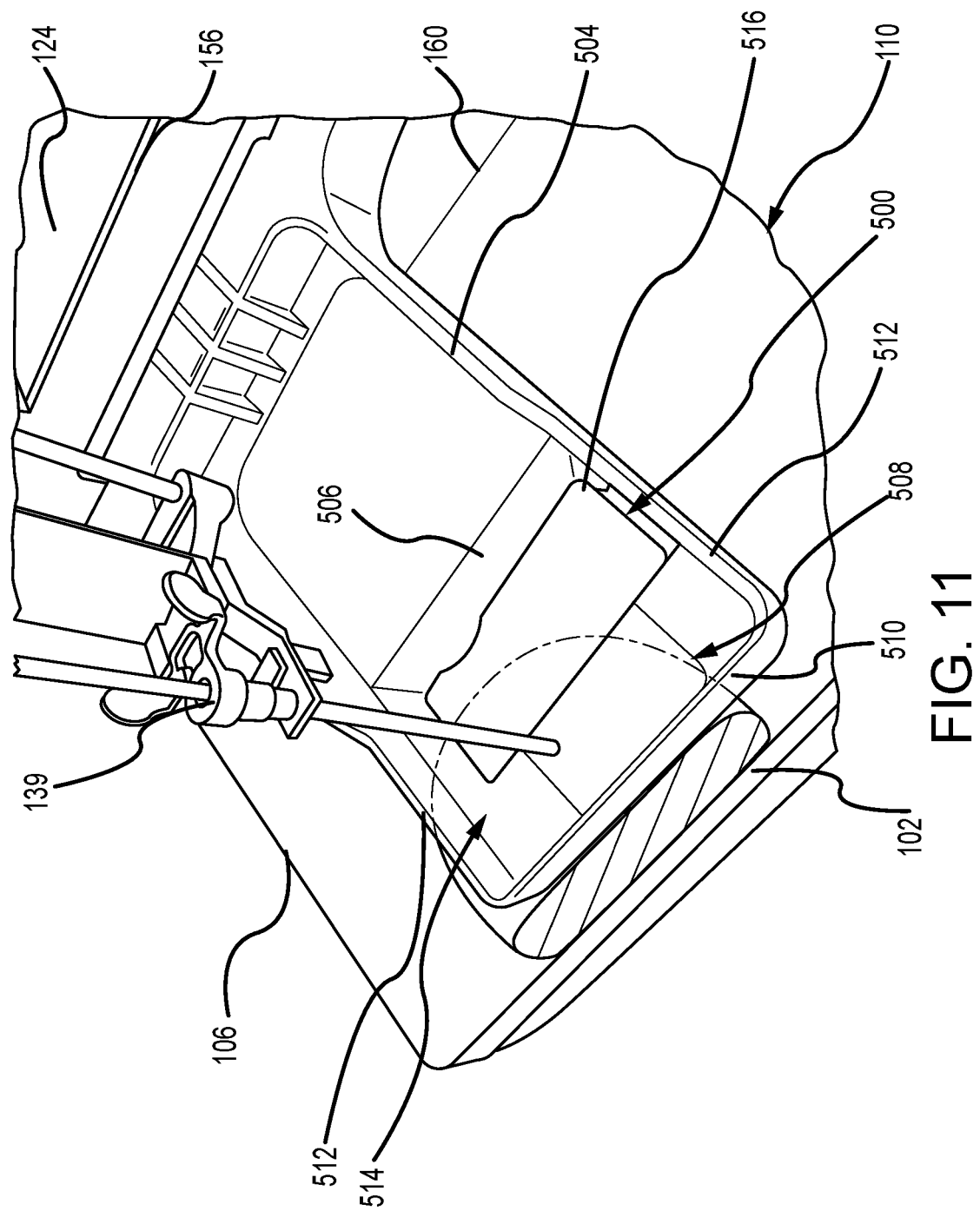
FIG. 11 is a perspective view of the support platform shown in FIG. 10 with the tissue specimen within the specimen container disposed on another compression paddle.
Figure 12:
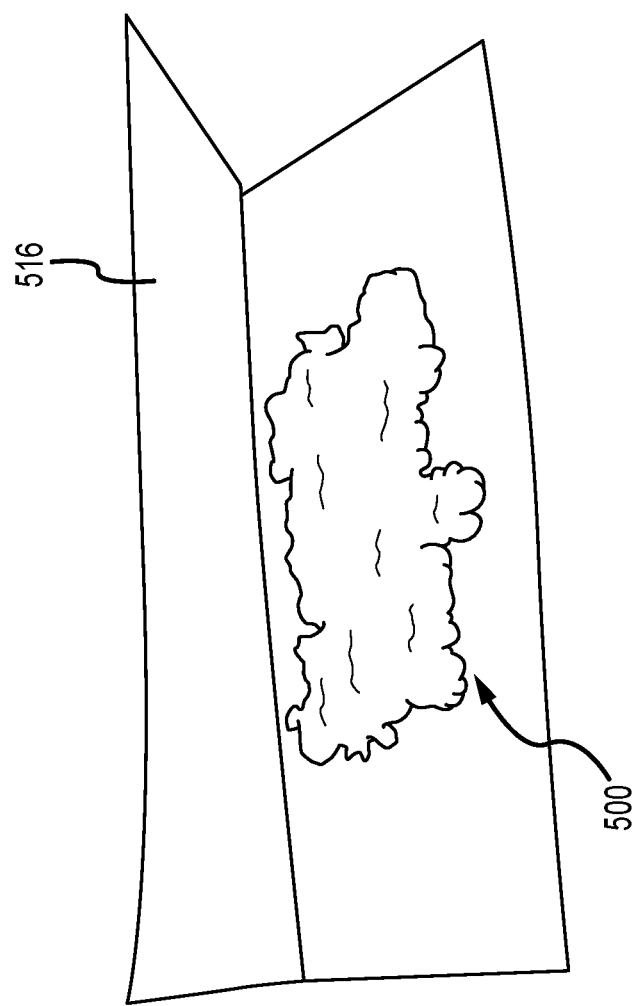
FIG. 12 is a perspective view of the tissue specimen within the specimen container of FIGS. 10 and 11.

FIG. 10 illustrates a larger (e.g., wider) compression paddle 502 when compared to the compression paddle 504 illustrated in FIG. 11. Different size compression paddles 502, 504 can be used for different size breasts 102 so as to increase patient comfort. Different size compression paddle 502, 504 may also be used for different area of interest locations. For example, FIG. 10 has an area of interest for the biopsy that is towards a middle of the patient's breast 102, while FIG. 11 has an area of interest that is towards an edge of the patient's breast 102. In the examples, each compression paddle 502, 504 has a compression plate 506 with a window 508 defined therein. Additionally, a front wall 510 and opposing side walls 512 may extend in an upward direction from the compression plate 506 and at least partially around a perimeter thereof. The compression plate 506 and walls 510, 512 define an upper volume 514 of the compression paddle 502, 504 that is open and accessible from above. The window 508 allows access to the patient's breast 102 during compression for biopsy procedures from the biopsy assembly 139.

In this example, once one or more tissue specimens 500 are obtained via the biopsy assembly 139, the tissue specimens 500 are placed in a specimen container 516 that is then placed within the upper volume 514 of the compression paddle 502, 504 and on top of the compression plate 506 for tissue specimen imaging. As illustrated in FIG. 12, the specimen container 516 is a radiolucent film that is configured to retain one or more tissue specimens 500 and enables the tissue specimens 500 to be moved by the technologists as required or desired. In another example, the specimen container 516 can be a radiolucent envelope. In other examples, the specimen container 516 may be a container produced by Faxitron Bioptics and as described above. In still other examples, the specimen container 516 may be any other container that enables tissue specimens 500 to be imaged as described herein. As illustrated in FIGS. 10 and 11, the size and shape of the specimen container 516 allows for the container to be placed on top of the compression paddle 502, 504 and within the imaging area 160 of the imaging system. While using the compression paddle 502, 504 lifts the specimen container 516 further above the x-ray receptor than the compression surface 110 (e.g., about the compression height of the patient's breast), the position of the tissue specimen 500 is still sufficient for tissue specimen imaging procedures. As such, the patient's breast 102 can remain compressed during tissue specimen imaging and the specimen imaging can be performed directly on the gantry of the imaging system post biopsy.

For tissue specimen imaging, the specimen container 516 may be placed on the left or right side of the compression plate 506 and between the window 508 and the side walls 512. As illustrated in FIG. 10, the container 516 is placed on the right side of the compression paddle 502, although, the container 516 may be alternatively or additionally placed on the right side of the compression paddle 502 as required or desired. In an aspect, the tissue specimens 500 within the specimen container 516 may be disposed adjacent the front wall 510 of the compression paddle 502. In another aspect, the tissue specimens 500 within the specimen container 516 may be offset from the front wall 510 and positioned towards the anterior side of the compression paddle 502. The specimen container 516 may alternatively or additionally be placed on an anterior side of the compression paddle 504 and as illustrated in FIG. 11. The compression paddle 504 in FIG. 11 is smaller than the compression paddle 502, and as such the left and right sides may not provide enough space for the specimen container 516. Thus, the specimen container 516 may be placed on the top of the compression plate 506 and on the anterior side of the window 508, opposite of the front wall 510. When the specimen container 516 is placed on the anterior side of the window 508, the tissue specimen 500 within the container 516 may be disposed proximate the left (as shown in FIG. 11) or right sidewall 512 as required or desired.

For tissue specimen imaging, the biopsy needle from the biopsy assembly 139 may be retracted or may remain extended. Tissue specimen imaging may be performed by a tomosynthesis imaging procedure or a mammography imaging procedure or any other imaging procedure as required or desired. The specimen container 516 may be completely supported on the compression plate 506 or may at least partially overhang the window 508. The tissue specimens 500 can be positioned over the patient's breast 102 or may be offset from the patient's breast 102. In any of the above configurations, tissue specimen imaging is enabled by locating the tissue specimens 500 on the compression paddle 502, 504. Additionally or alternatively, the x-ray source can include two, three, or more focal spot sizes as described herein to increase resolution of the tissue specimen images.

In this example, the placement of the specimen container 516 on the compression paddle 502, 504, is within the imaging area 160 of the imaging system so that duplicate imaging components are not needed on the gantry. Additionally, the specimen imaging filter 152 (shown in FIGS. 3 and 4) may have corresponding apertures so that the path of the x-ray beam is directed to the tissue specimens 500 disposed on the compression paddle 502, 504. By placing the specimen container 516 at various locations on the compression paddle 502, 504, the tissue specimen 500 can also be located in areas without attenuated radiation generated from the x-ray images of the patient's breast 102.

Figure 13:
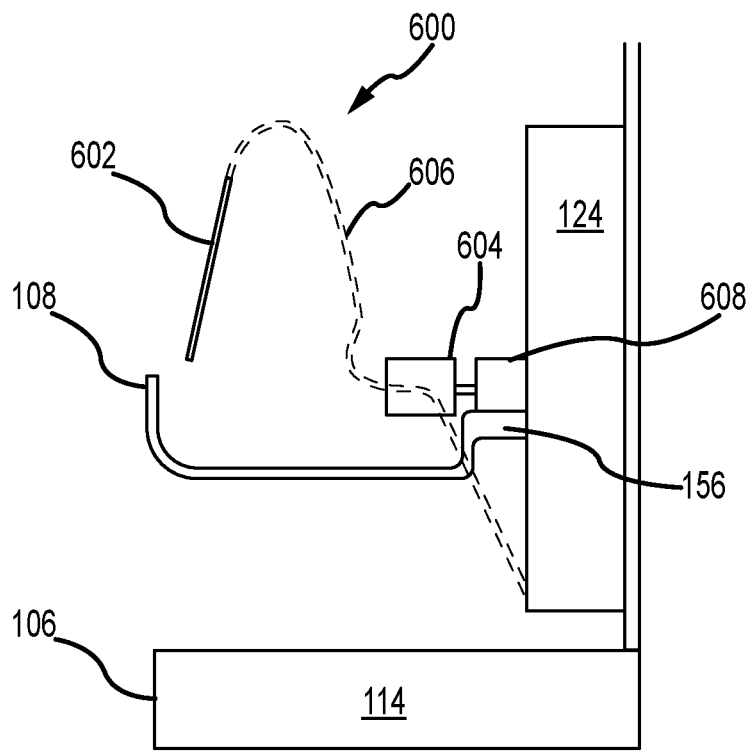
FIG. 13 is a schematic view of the support platform of the imaging system shown in FIGS. 1 and 2 with an exemplary vacuum assisted biopsy assembly.

FIG. 13 is a schematic view of the support platform 106 of the imaging system 100 (shown in FIGS. 1 and 2) with an exemplary vacuum assisted biopsy assembly 600. As described above, the support platform 106 houses the x-ray receptor 114 and extends from the support arm 124 that also supports the compression paddle 108. The support platform 106 is used to compress and immobilize the patient's breast with the compression paddle 108. A paddle bracket 156 can releasably couple the compression paddle 108 to the support arm 124 and enable the compression paddle to move (e.g., up and down) relative to the support platform 106 so as to compress the patient's breast.

Additionally, coupled to the support arm 124 is the vacuum assisted biopsy assembly 600. The biopsy assembly 600 includes an excision tool 602 coupled to a tissue reservoir 604 via a sample transport system 606 (e.g., tubing). The sample transport system 606 is also coupled to a vacuum source (not shown) so that in operation a tissue specimen may be obtained via the excision tool 602 and the tissue specimen can be moved automatically to the tissue reservoir 604. In some examples, a fluid such as saline may be used to lavage the breast cavity during excision, and to vent the tissue sample to facilitate transport along the sample transport system 606. In the example, the tissue reservoir 604 is coupled to the support arm 124 by a bracket 608. In some examples, the bracket 608 may be configured to couple to the compression paddle 108 and/or the paddle bracket 156. In other examples, the bracket 608 may be integral with the paddle bracket 156.

Figure 14:
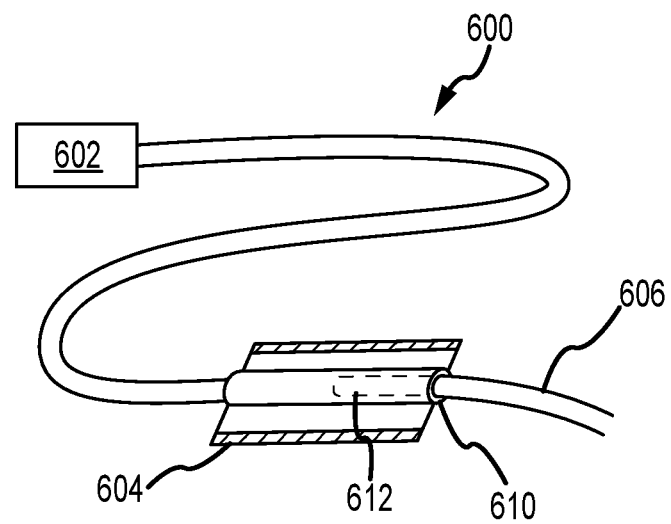
FIG. 14 is an enlarged view of a tissue reservoir of the vacuum assisted biopsy assembly shown in FIG. 13.
Figure 15:
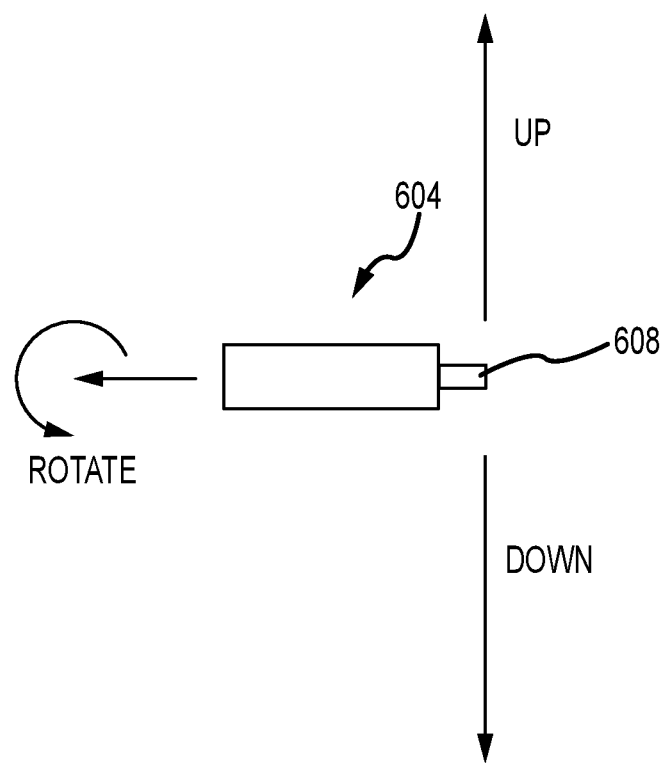
FIG. 15 is a schematic view of the tissue reservoir shown in FIG. 14.

FIG. 14 is an enlarged view of the tissue reservoir 604 of the vacuum assisted biopsy assembly 600. FIG. 15 is a schematic view of the tissue reservoir 604. Referring concurrently to FIGS. 14 and 15, at the tissue reservoir 604, the sample transport system 606 includes a filter mesh 610 that is configured to capture a tissue specimen 612 at the tissue reservoir 604 while allowing fluid to flow within the sample transport system 606. In operation, the patient's breast is immobilized and the excision tool 602 is used to extract the tissue specimen 612. Once the tissue specimen 612 is excised, the tissue specimen 612 is captured at the tissue reservoir 604 via the filter mesh 610 along the sample transport system 606. The captured tissue specimen 612 can then be imaged at the gantry of the imaging system. Because the tissue reservoir 604 is coupled to the support arm 124 (shown in FIG. 13), the bracket 608 is configured to enable the tissue reservoir 604 to move up and/or down relative to the x-ray source (not shown), and/or rotate as required or desired, and as illustrated in FIG. 15. This movement of the tissue reservoir 604 allows for the tissue specimen 612 to be more easily imaged on the gantry.

In some examples, the tissue reservoir 604 is configured to secure and at least partially compress the tissue specimen 612 so that the tissue specimen 612 does not move within the sample transport system 606 during movement of the tissue reservoir 604. During imaging of the tissue specimen 612, the patient's breast may be released from the gantry as required or desired. Additionally or alternatively, the x-ray source can include two, three, or more focal spot sizes as described herein to increase resolution of the tissue specimen images.

This disclosure describes some examples of the present technology with reference to the accompanying drawings, in which only some of the possible examples were shown. Other aspects can, however, be embodied in many different forms and should not be construed as limited to the examples set forth herein. Rather, these examples were provided so that this disclosure was thorough and complete and fully conveyed the scope of the possible examples to those skilled in the art. Any number of the features of the different examples described herein may be combined into one single example and alternate examples having fewer than or more than all of the features herein described are possible. It is to be understood that terminology employed herein is used for the purpose of describing particular examples only and is not intended to be limiting. It must be noted that, as used in this specification, the singular forms "a," "an," and "the" include plural referents unless the context clearly dictates otherwise.

Although specific examples were described herein, the scope of the technology is not limited to those specific examples. One skilled in the art will recognize other examples or improvements that are within the scope of the present technology. Therefore, the specific structure, acts, or media are disclosed only as illustrative examples. Examples according to the technology may also combine elements or components of those that are disclosed in general but not expressly exemplified in combination, unless otherwise stated herein. The scope of the technology is defined by the following claims and any equivalents therein.

The invention claimed is:

1. An x-ray breast imaging system comprising:
   a breast support platform comprising an x-ray receptor; and
   an x-ray tube head comprising:
      an x-ray source configured to emit an x-ray beam in a direction towards the x-ray receptor;
      a collimator;
      a filter assembly comprising a plurality of filter slots selectively positionable adjacent to the collimator; and
      a specimen imaging filter disposed within a slot of the plurality of filter slots, wherein the specimen imaging filter comprises at least one aperture defined therein, and wherein the specimen imaging filter blocks a portion of the emitted x-ray beam so that the at least one aperture defines a path of the emitted x-ray beam towards the x-ray receptor.

2. The x-ray breast imaging system of claim 1, wherein the at least one aperture is substantially rectangular-shaped.

3. The x-ray breast imaging system of claim 1, wherein the specimen imaging filter is formed from lead material.

4. The x-ray breast imaging system of claim 1, wherein the at least one aperture comprises a pair of apertures.

5. The x-ray breast imaging system of claim 4, wherein the collimator comprises at least one collimator blade, and wherein the at least one collimator blade is configured to selectively cover one of the pair of apertures.

6. The x-ray breast imaging system of claim 1, wherein the filter assembly comprises a rotatable filter wheel having the plurality of filter slots.

7. The x-ray breast imaging system of claim 1, wherein the x-ray source comprises three or more focal spot sizes.

8. The x-ray breast imaging system of claim 7, wherein one of the focal spot sizes is less than or equal to 50 µm.

9. The x-ray breast imaging system of claim 1, further comprising a specimen container configured to retain one or more tissue specimens.

10. The x-ray breast imaging system of claim 9, wherein the specimen container is removably coupleable to the imaging system and independently rotatable relative to the x-ray tube head.

11. The x-ray breast imaging system of claim 1, wherein the at least one aperture defines the path of the emitted x-ray beam that corresponds to a specific area on the breast support platform.

12. The x-ray breast imaging system of claim 1, further comprising a compression paddle configured to compress a patient's breast against the breast support platform, and wherein the at least one aperture defines the path of the emitted x-ray beam that corresponds to a specific area on the compression paddle.

13. The x-ray breast imaging system of claim 1, further comprising a vacuum assisted biopsy assembly coupled to the imaging system, wherein the vacuum assisted biopsy assembly comprises a reservoir configured to capture a tissue specimen.

14. The x-ray breast imaging system of claim 1, further comprising a high energy acquisition filter formed from copper.

15. A method of acquiring a tissue specimen image on an x-ray breast imaging system, the method comprising:
   compressing a patient's breast between a compression paddle and a support platform;
   imaging the patient's breast via an x-ray source disposed in an x-ray tube head and an x-ray receptor disposed in the support platform;
   obtaining one or more tissue specimens from the patient's breast;

retaining the one or more tissue specimens in a container;

imaging the one or more tissue specimens via the same x-ray source and x-ray receptor used for imaging the patient's breast, wherein the imaging includes blocking a portion of an emitted x-ray beam from the x-ray source by a specimen imaging filter within the x-ray tube head so that at least one aperture within the specimen imaging filter defines a path of the emitted x-ray beam towards the x-ray receptor.

16. The method of claim 15, wherein blocking a portion of an emitted x-ray beam further comprises covering one aperture of a pair of apertures via at least one collimator blade of a collimator.

17. The method of claim 15, wherein imaging the patient's breast and imaging the one or more tissue specimens are performed under the same breast compression procedure.

18. The method of claim 15, further comprising placing the container on the support platform and within an imaging area that corresponds to the x-ray receptor disposed within the support platform.

19. The method of claim 18, wherein placing the container on the support platform comprises placing the container within a right anterior area of the imaging area or within a left anterior area of the imaging area.

20. The method of claim 15, further comprising placing the container on the compression paddle.

21. The method of claim 15, wherein obtaining one or more tissue specimens comprises excising the one or more tissue specimens via a vacuum assisted biopsy device, and wherein retaining the one or more tissue specimens comprises capturing the one or more tissue specimens in a reservoir.

22. The method of claim 21, wherein the reservoir is independently moveable relative to the x-ray source and the x-ray receptor.

23. The method of claim 15, wherein imaging the patient's breast occurs at a first focal spot size of the x-ray source and imaging the one or more tissue specimens occurs at a second focal spot size, and wherein the first focal spot size is greater than the second focal spot size.

* * * * *